(12) United States Patent
Stoll et al.

(10) Patent No.: US 9,555,134 B2
(45) Date of Patent: Jan. 31, 2017

(54) MANGANESE-OXO CLUSTERS AS CONTRAST AGENTS FOR MAGNETIC RESONANCE IMAGING

(75) Inventors: Sarah Stoll, Washington, DC (US); Julie Mertzman, Washington, DC (US); Edward Van Keuren, Herndon, VA (US); Christopher Albanese, Pelham Manor, NY (US); Stanley Fricke, New Market, MD (US)

(73) Assignee: Georgetown University, Washington, DC (US)

( * ) Notice: Subject to any disclaimer, the term of this patent is extended or adjusted under 35 U.S.C. 154(b) by 41 days.

(21) Appl. No.: 13/125,244

(22) PCT Filed: Oct. 21, 2009

(86) PCT No.: PCT/US2009/061452
§ 371 (c)(1),
(2), (4) Date: Dec. 16, 2011

(87) PCT Pub. No.: WO2010/048268
PCT Pub. Date: Apr. 29, 2010

(65) Prior Publication Data
US 2012/0134932 A1 May 31, 2012

Related U.S. Application Data

(60) Provisional application No. 61/196,725, filed on Oct. 21, 2008.

(51) Int. Cl.
| | | |
|---|---|---|
| *A61K 49/00* | (2006.01) | |
| *A61K 49/18* | (2006.01) | |
| *B82Y 5/00* | (2011.01) | |
| *A61K 49/12* | (2006.01) | |

(52) U.S. Cl.
CPC ............. *A61K 49/128* (2013.01); *A61K 49/00* (2013.01); *A61K 49/1878* (2013.01); *B82Y 5/00* (2013.01)

(58) Field of Classification Search
None
See application file for complete search history.

(56) References Cited

U.S. PATENT DOCUMENTS

| | | |
|---|---|---|
| 5,330,742 A | 7/1994 | Deutsch et al. |
| 5,648,124 A * | 7/1997 | Sutor ........................... 427/475 |
| 2005/0265923 A1* | 12/2005 | Toner .................. A61K 49/048 424/1.11 |

OTHER PUBLICATIONS

Vestal, C.R., et al., "Atom Transfer Radical Polymerization Synthesis and Magnetic Characterization of MnFe2O4/Polystyrene Core/Shell Nanoparticles", 2002, JACS, pp. 14312-14313.*

(Continued)

*Primary Examiner* — Michael G Hartley
*Assistant Examiner* — Lance Rider
(74) *Attorney, Agent, or Firm* — Klarquist Sparkman, LLP

(57) ABSTRACT

Nanoparticles for use as magnetic resonance imaging contrast agents are described. The nanoparticles are made up of a polymeric support and a manganese-oxo or manganses-iron-oxo cluster having magnetic properties suitable of a contrast agent. The manganese-oxo clusters may be Mn-12 clusters, which have known characteristics of a single molecule magnet. The polymer support may form a core particle which is coated by the clusters, or the clusters may be dispersed within the polymeric agent.

7 Claims, 13 Drawing Sheets

(56) References Cited

OTHER PUBLICATIONS

Braybrook, J.H., et al., "Paramagnetic Particulates as Contrast Agents for Magnetic Resonance Imaging (MRI)", 1991, Polymer International, pp. 251-259.*

Gupta, A.K., et al., Synthesis and surface engineering of iron oxide nanoparticles for biomedical applications, 2005, Biomaterials, pp. 3995-4021.*

Schake, A.R., et al., "High-Spin Molecules: Iron(III) Incorporation into [Mn12O12(02CMe)16(H20)4] to Yield [MnsFe4O12(02CMe)16(H20)4] and Its Influence on the S=10 Ground State of the Former", 1994, Inorg. Chem, pp. 6020-6028.*

Berkowitz, B.A., et al., "Manganese-Enhanced MRI Studies of Alterations of Intraretinal Ion Demand in Models of Ocular Injury", 2007, Invest Opthalmol Vis Sci., pp. 3796-3804.*

Clemente-Leon, M., et al., "Incorporation of Mn12 single molecule magnets into mesoporous silica", J. Mater. Chem., 2003, pp. 3089-3095.*

Santa Maria, L.C., et al., "Preparation and characterization of manganese, nickel and cobalt ferrites submicron particles in sulfonated crosslinked networks", Polymer, 2005, pp. 11288-11293.*

Edward Van Keuren, Maki Nishida, Sarah Stoll, Julie Mertzman;Multifunctional Nanoscale Materials for the $21^{st}$ Century; International Symposium at The Center for Nanoscale Materials; Mar. 6-7, 2009; pp. 33-35; Argonne National Laboratory; Argonne, IL USA.

Mertzman, J.E. et al., "Surface attached manganese-oxo clusters as potential contrast agents," Chem. Commun., 2009, 788-790.

Schake, A.R. et al., "Variation in the Electron Count and Ground State of [Mn12O12(O2CR)16(H2O)4] (R=Me or Ph) by Metal Substitution and Redox Changes: Preparation and Properties of [Mn8Fe4O2(O2CMe) 6(H2O)4]4H2O2MeCO2H and [NPrn4][Mn2O2(O2CPh)6(H2O)4]H2O," J. Chem. Soc., Chem. Commun., 1992, 181-183.

Steckel, J. S. et al., "Monolayer and Multilayer Films of [Mn12O12(O2CMe)16]," Nano Lett., 2004. vol. 4, No. 3, pp. 399-402.

Palacio, F. et al., "Magnetic behaviour of a hydrid polymer obtained from ethyl acrylate and the magneti cluster Mn12O12(acylage)16," J. Mater. Chem., 2004, vol. 14, pp. 1873-1878.

Ruiz-Molina, D. et al., "Characterisation of nanoscopic [Mn12O12 (O2CR) 16(H2O)4] single-molecule magnets: physicochemical properties and LDI- and MALDI-TOF mass spectrometry," J. Mater. Chem., 2002, vol. 12, pp. 1152-1161.

* cited by examiner

MANGANESE-OXO CLUSTERS AS CONTRAST AGENTS FOR MAGNETIC RESONANCE IMAGING

STATEMENT OF PRIORITY

This application claims priority to U.S. Provisional Patent Application No. 61/196,725, filed Oct. 21, 2008 the disclosure of which is hereby incorporated by reference herein.

STATEMENT OF GOVERNMENT FUNDING

This work was supported in part by grants DMR-0304273 and CHE-05522586 from the National Science Foundation. The U.S. government has certain rights in this invention.

FIELD OF THE INVENTION

The present invention relates to contrast agents for enhancing magnetic resonance imaging. The agents of the present invention are particles containing metal-oxo clusters.

BACKGROUND OF THE INVENTION

Magnetic resonance imaging (MRI) has become a widely used tool for medical imaging and research. As a medical imaging technique, MRI is preferred by patients as it does not require exposure to ionizing radiation. Further, MRI has proven to be the best way to obtain images of soft tissues in the body. Because MRI can be used for imaging soft tissues, it can be effectively used to determine if a tumor or other lesion has developed in an organ and to determine structural changes in the brain, along with a multitude of other uses.

Very briefly. MRI requires placing the patient to be imaged in a strong magnetic field. The magnetic field causes the hydrogen nuclei to align so that they are spinning either parallel or antiparallel to the magnetic field. A radiofrequency (RF) pulse is then applied that excites the spinning hydrogen nuclei out of alignment. After application of the RF pulse, the excited nuclei relax back to alignment with the magnetic field, emitting RF signals that are detected by the MRI apparatus. Detection of the RF signals is used to calculate both the longitudinal relaxation time ($T_1$) and transverse relaxation time ($T_2$), which are used to form images of the patient.

The primary limitation of MRI is its sensitivity. Contrast agents are often administered to the patient before imaging overcome sensitivity limitations. These contrast agents cause changes in $T_1$ and $T_2$ for surrounding hydrogen nuclei, which helps clearly differentiate structures in the MRI image.

One class of contrast agents is the positive contrast agents, which decrease $T_1$ and $T_2$ to a similar extent and are typically used in obtaining $T_1$ weighted images. Positive contrast agents cause a tissue structure associated with the contrast agent to appear brighter on an MRI image, making these agents very useful for increasing MRI specificity.

A majority of the positive contrast agents approved by the Food and Drug Administration (FDA) contain the paramagnetic metal ion gadolinium. Although free $Gd^{3+}$ is toxic, it can be ligand protected to greatly reduce its bioavailability. While Gd containing contrast agents are generally considered safe for administration to humans, recently concerns have arisen due to the possible causal connection between Gd contrast agents and the formation of nephrogenic systemic fibrosis in patients with renal disfunction. Because of this, physicians are now debating the risks of administering Gd contrast agents to certain types of patients, and the FDA has requested the manufacturers of Gd constrast agents to add new warning information to their labels (H. Steen and V. Schwenger, *Pediatr Nephrol,* 2007, 22, 1239; www.fda.gov/cder/drug/infopage/gcca/qa_200705.htm).

There is also an environmental concern with the use of Gd contrast agents, as their impact on the environment after excretion by the patient is largely unknown. As the popularity of MRI continues to increase, more and more Gd contrast agents will be used, meaning that more Gd will be released into the environment.

Because of the possible health and environmental concerns related to the use of Gd contrast agents, it is desirable to develop contrast agents using metals that are better tolerated both by the body and the environment. One metal that has paramagnetic properties making it suitable for use as an MRI contrast agent while also being more benign to health and the environment is manganese. However, the toxicity of free Mn metal has limited the development of Mn contrast agents (A. Koretsky and A. Silva, *NMR in Biomedicine,* 2004, 17, 527). A Mn contrast agent, manganese dipyrodoxaldiphosphate (Mn-DPDP), has been approved by the FDA as safe for human use and is sold by GE Healthcare under the name Teslascan™. However, Mn-DPDP has only been approved for imaging of the liver and has shown only limited effect on $T_1$ and $T_2$ in tissues outside of liver and kidney (G. Elizondo et al., *Radiology,* 1991, 178, 73).

U.S. Pat. Nos. 5,330,742 and 5,548,870 to Deutsch et al., describe paramagnetic metal cluster compounds for enhancing MRI. However, the reduced metal cluster described, $Z^+[Mn_{12}X_{12}(OYR)_{16}(L)_4]$, is highly reactive and has not been demonstrated to be stable in biological systems because it would react immediately in water. Also, as this cluster is insoluble in water, it must be conjugated to a carrier in order to be delivered as a contrast agent. Although the patents describe conjugating this reactive cluster to polymeric or microspheric carriers, liposome carries and hydroxyapatite carriers, these carriers only provide for limited increases in the solubility of the cluster. Further, the conjugation of the $Z^+[Mn_{12}X_{12}(OYR)_{16}(L)_4]$ cluster is unlikely to make it more suitable for use in a biological system.

U.S. Pat. No. 5,364,953 to Beaty et al. describes paramagnetic metal clusters having oxygen and/or nitrogen containing ligands for use as MRI contrast agents. However, the metal clusters taught in the patent are not more than sparingly soluble in water and precipitate from solution over time.

As such, there remains a need in the art for a highly water soluble and bio-stable contrast agent that provides high specificity while also being benign to the body and the environment.

SUMMARY OF THE INVENTION

It is an object of the present invention to provide contrast agents for magnetic resonance imaging having nanoparticles made up of a polymer support and a manganese-oxo cluster. The manganese-oxo cluster may contain from 2 to 12 manganese ions, and may have Mn(III) and/or Mn(IV) ions.

It is a further object of the present invention to provide contrast agents for magnetic resonance imaging having nanoparticles that contain manganese-oxo clusters of the general formula $[Mn_{12}O_{12}(O_2CR)_{16}(H_2O)_4]$, where R may be an alkyl, vinyl, halo, oxy, or oxyalkyl group.

It is a further object of the present invention to provide contrast agents for magnetic resonance imaging having nanoparticles that contain manganese-iron-oxo clusters of the general formula [Mn$_8$Fe$_4$(O$_2$R)$_{16}$(H$_2$O)$_4$], where R may be an alkyl, vinyl, halo, oxy, or oxyalkyl group.

It is a further object of the present invention to provide contrast agents for magnetic resonance imaging having nanoparticles that contain manganese-iron-oxo clusters of the general formula [Mn$_8$Fe$_4$O$_{12}$(O$_2$R)$_{16}$(H$_2$O)$_4$], where R may be an alkyl, vinyl, halo, oxy, or oxyalkyl group.

It is a further object of the present invention to provide contrast agents for magnetic resonance imaging having a polymer with a monomeric unit of the general formula:

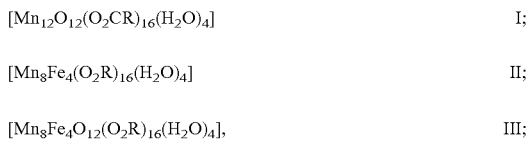

where R is an organic side chain, and L is a carboxylic acid.

It is a still further object of the present invention to provide a method for making a contrast agent for magnetic resonance imaging having the steps of: providing a first solution of a polymeric nano-bead having carboxylate groups on its surface in an alcohol; providing a second solution of a manganese-oxo compound of the general formula I or a manganese-iron-oxo compound of the general formulas II or III in the alcohol:

[Mn$_{12}$O$_{12}$(O$_2$CR)$_{16}$(H$_2$O)$_4$]    I;

[Mn$_8$Fe$_4$(O$_2$R)$_{16}$(H$_2$O)$_4$]    II;

[Mn$_8$Fe$_4$O$_{12}$(O$_2$R)$_{16}$(H$_2$O)$_4$],    III;

where R may be an alkyl, vinyl, halo, oxy, or oxyalkyl; mixing the first solution and the second solution; stirring the mixture for an amount of time sufficient for substantially all of the carboxylate groups to react with the manganese-oxo compound; and isolating the resultant polymeric beads covered in a layer of manganese-oxo compound.

It is yet a further object of the present invention to provide a method for making a contrast agent for magnetic resonance imaging having the steps of: providing a first solution containing a compound of the general formula IV:

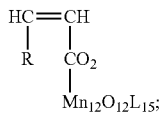

where L may be an organic side chain; and where R may be any carboxylic acid; providing a second solution containing a compound of the general formula V:

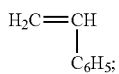

mixing the first solution with the second solution; adding a polymerization initiation agent; and reacting the mixture for an amount of time sufficient to cause completion of the reaction to form a polymer having a monomeric unit of the general formula VI:

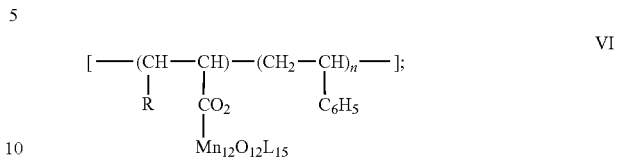

L may be an organic side chain; and where R may be any carboxylic acid.

The present invention provides a method to obtain magnetic resonance images of cells, tissues, animals and human subjects. It is yet a further object of the present invention to provide a method for obtaining a magnetic resonance image of a subject by administering to the subject the a sufficient amount of the contrast agents of the present invention in order to obtain a magnetic resonance image with the desired contrast, allowing a sufficient amount of time for the contrast agent to migrate throughout the subject, and obtaining a magnetic resonance image of the subject.

DETAILED DESCRIPTION OF THE INVENTION

Figure 1:
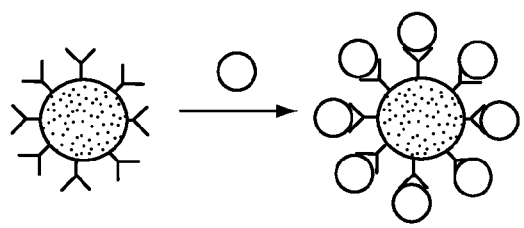
FIG. 1 shows a schematic of the attachment of Mn-12 to carboxylate coated nano-beads. The nano-beads are shown in black and the Mn-12 in gray.

Nanoparticles containing manganese-oxo clusters for use as MRI contrast agents are described herein. In one embodiment, the nanoparticles of the present invention have a polymer support with Mn-oxo or Mn—Fe-oxo clusters attached to the support. The metal-oxo clusters used in the forming the nanoparticles of the present invention have magnetic properties that make them suitable for use as MRI contrast agents. In certain embodiments, the nanoparticles of the present invention are from about 5 to about 1000 nm, about 5 to about 500 nm, about 5 to about 100 nm, about 5 to about 50 nm in diameter.

In certain embodiments of the invention, the Mn-oxo clusters are Mn-12 clusters. The Mn-12 clusters of the present invention may have a general formula $[Mn_{12}O_{12}(O_2CR)_{16}(H_2O)_4]$, where R may be an alkyl, vinyl, halo, oxy, oxyalkyl group. Mn-12 is considered the prototypical 'Single Molecule Magnet' (SMM) (T. L is, *Acta Crystallogr. Sect. B.* 1980, 36, 2042; A. Barra et al., *J. Am. Chem. Soc,* 1991, 113, 5873; R. Sessoli et al. *Nature,* 1993, 365, 141), meaning that the Mn-12 cluster acts as a nanoscale individual magnet. The high spin state (S=10) and anisotropy of Mn-12 clusters results in striking magnetic properties (G. Christou et al., *MRS Bulletin,* 2000, November, 66). The clusters are typically mixed valent and are made up of a tetrahedron of Mn (IV) ions, surrounded by eight Mn (III) ions, although other combinations of valencies may also be used in the present invention. In certain embodiments of the invention, the Mn-12 cluster is $[Mn_{12}O_{12}(O_2CCH_3)_{16}(H_2O)_4]$. In other embodiments of the invention, the Mn-12 cluster is $[Mn_{12}O_{12}(O_2CC_6H_4CH=CH_2)_{16}(H_2O)_4]$.

Mn-12 clusters have properties which make them ideal as MRI contrast agents. The clusters have a very high spin state (high paramagnetic susceptibility), they are easily derivatized with a variety of ligands, and they have 4 waters that are intimately associated with the clusters that are exchanged rapidly on an MRI timescale, because of their coordination with labile Mn (III) ions (H. Eppley et al., *J. Am. Chem. Soc.,* 1995, 117, 301). However, Mn-12 clusters by themselves have poor water solubility, forming a flocculent material within minutes upon dissolution in water. The present invention overcomes the solubility problems of Mil-12 by incorporating Mn-12 into nanoparticles that are soluble in water.

In other embodiments of the invention, other Mn-oxo clusters may be used. For example, clusters having 2-12 Mn ions may be used in embodiments of the present invention. The clusters may be made up of either Mn(UI) or Mn(IV) ions, or may have both Mn(III) and Mn(IV) ions in the same cluster. Examples of other Mn-oxo clusters that are contemplated for use in the present invention include tetranuclear Mn-oxo clusters described by Dube et al. (*J. Am. Chem. Soc,* 1998, 120, 3704) and Chen et al. (*Inorg. Chem.,* 2005, 44, 9567).

In other embodiments of the present invention, the metal-oxo clusters used are Mn—Fe-oxo clusters, which have both manganese and iron centers. The Mn—Fe-oxo clusters of the present invention may have a general formula $[Mn_8Fe_4(O_2R)_{16}(H_2O)_4]$, where R may be an alkyl, vinyl, halo, oxy, or oxyalkyl group. In certain embodiments, the Mn—Fe-oxo clusters of the present invention may have general formula $[Mn_8Fe_4O_{12}(O_2R)_{16}(H_2O)_4]$, where R may be an alkyl, vinyl, halo, oxy, or oxyalkyl group.

It is also contemplated that Mn—Fe-oxo clusters having other ratios of manganese to iron centers may be used in the present invention. The Mn—Fe-oxo clusters, when conjugated as described herein, are water soluble, stable and show significant relaxivity. In certain embodiments of the invention, the Mn—Fe-oxo cluster is $[Mn_8Fe_4(O_2CH_3)_{16}(H_2O)_4]$. In certain embodiments of the invention, the Mn—Fe-oxo cluster is $[Mn_8Fe_4O_{12}(O_2CCH_3)_{16}(H_2O)_4]$.

It is further contemplated that the clusters of the present invention may exist in solvated form, such as in water solvated form, acetic acid solvated form or in other solvate forms well known in the art. As a non-limiting example, an embodiment of the invention includes the solvated Mn—Fe-oxo cluster $[Mn_8Fe_4(O_2CH_3)_{16}(H_2O)_4] \cdot 4H_2O \cdot 2CH_3COOH$. In a specific embodiment, the solvated Mn—Fe-oxo cluster has the formula $[Mn_8Fe_4O_{12}(O_2CCH_3)_{16}(H_2O)_4] \cdot 4H_2O \cdot 2CH_3COOH$.

In certain embodiments of the invention, the polymer support is a pre-formed polymer bead. The polymer bead may be made of styrene, vinyl benzoic acid, vinyl alcohol, latex, or co-polymers thereof. In certain embodiments, the pre-formed polymer beads are surface coated with a carboxylate or other functional group that allows for facile attachment of the Mn-oxo clusters. In one embodiment of the present invention, the pre-formed polymer beads are Polybead® Carboxylate Microspheres sold by Polysciences, Inc. of Warrington, Pa. In other embodiments, porous silicon nanoparticles may be used, such as Mobil Composition of Matter 41 (MCM-41), available from ExxonMobil Chemical Company of Houston. Tex. MCM-41 nanoparticle are useful carriers as they are benign in the body and have a high surface area for attaching clusters. Further, the MCM-41 nanoparticles seem to enhance to relaxivity effects of the clusters.

If carboxylate coated polymer beads are used, the metal-oxo clusters may be attached to the beads using the method described by Steckel et al. (*Nano Lett.,* 2004, 4, 399), which is hereby incorporated by reference herein. A general schematic of this procedure is shown in FIG. 1. Generally, a solution of carboxylate coated polymer beads in ethanol is mixed with a solution of metal-oxo cluster in ethanol. The mixture is allowed to stir for a period of time sufficient to cause the metal-oxo clusters to coat the polymer beads. The metal-oxo coated nanoparticles are then isolated and washed, at which point they are ready to be made into a preparation for administration to a patient. Further descriptions of forming metal-oxo coated polymer beads are shown in the examples below.

In certain other embodiments of the present invention, the polymer support is formed as a co-polymer with the metal-oxo clusters. The co-polymers may be made with one or more of styrene, vinyl benzoic acid, vinyl alcohol or latex. The co-polymers may be formed into nanoparticles during polymerization or may be formed into a nanoparticle structure after polymerization is complete.

In one embodiment of the present invention, the co-polymer is formed from Mn12 vinyl benzoic acid (Mn12-BVA) and styrene as shown in Scheme 1, where R is an organic side chain and L is $O_2CH=CH-R$ or any carboxylic acid.

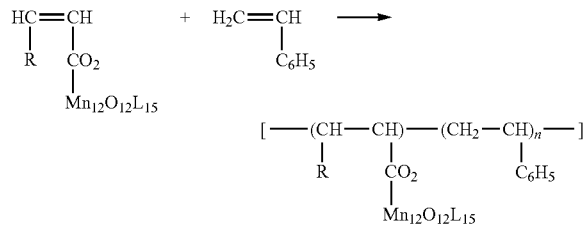

In forming co-polymers, a wide range of organic side chains can be used, as are well known in the art, including, but not-limited to, alkanes, alkenes, alkynes, alcohols, halogens, ketones, aldehydes, carboxylic acids and ethers. In certain embodiments of the present invention, R may be a $C_1$-$C_6$ alkane.

After the co-polymers are formed into nanoparticles, isolated and washed, they are ready to be made into a preparation for administration to the patient. Further descriptions of forming co-polymers can be found in the examples below.

In certain embodiments of the invention, the nanoparticles are formed so that free manganese is not released from the particles into solution. The nanoparticles may stay intact so that they do not release free manganese until after they are excreted from the body.

In certain embodiments of the present invention, the nanoparticles may be modified on their surface. Such modifications may be used to specifically target the nanoparticles to certain areas of the body. For example, the nanoparticles may be modified with peptides, sugars, antibodies, ligands, dendrimers, nucleic acids or synthetic ligands that cause the nanoparticle to be transported to or to remain in a higher concentration in a specific tissue structure. The nanoparticles may also be modified with chemical groups that increase or decrease their solubility as needed.

Once metal-oxo nanoparticles are synthesized, they can be made into a preparation for administration to the patient to be imaged. In certain embodiments of the invention, the nanoparticles are suspended into a solution suitable for intravenous administration. Such a solution may be a suspension in pure water, or the solution may contain salts or other compounds which are suitable for intravenous administration. If intravenous administration is used, the nanoparticle preparation may be administered all at once as a bolus, or may be administered through an intravenous drip over a period of minutes to hours. In other embodiments of the invention, the nanoparticles may be formulated into preparations suitable for oral administration.

Once the nanoparticles of the present invention have been administered to the patient in a sufficient amount and a sufficient amount of time has passed for the nanoparticles to migrate to the tissues desired to be imaged, an MRI can be performed on the patient as is well known in the art. In certain embodiments, $T_1$ weighted images may be obtained, although it is also contemplated that $T_2$ and $T_3$* weighted images may also be obtained.

The nanoparticles and methods of the present invention may be used with any type of tissue that is suitable for imaging by MRI. In certain embodiments, the type of tissue may be organs, glands, nodes, connective tissues, muscle tissues, nervous tissues, epithelial tissues, bones, tumors, both malignant and non-malignant, and other growths. The nanoparticles and methods of the present invention may also be used with a single cell or group of cells derived from any tissue suitable for imaging by MRI.

The patients, or subjects in which the nanoparticles and methods of the present inventions can be used are preferably humans. However, it is also contemplated that the nanoparticles and methods of the present invention may be used in any animal for which MRI can be performed. These subjects include mammals, such as domestic animals, veterinary animals, research animals and livestock. Specific examples include, but are not limited to dogs, cats, horses, mice, rats, hamsters, gerbils, apes, monkeys, rabbits, cattle, pigs and poultry such as chickens and turkeys.

The nanoparticles and methods of the present invention may also be used in the imaging of tissues or cells in isolation. The tissues and cells to be imaged may have been removed from a subject through surgery, biopsy or other procedure. The tissues and cells to be imaged may also have been grown in culture as is well known in the art. Along with being useful for medical diagnostic imaging of tissues and cells, the nanoparticles and methods of the present invention may be used for research purposes.

In specific embodiments, the methods of the present invention involve adding a sufficient amount of a contrast agent described herein to a cell or tissue in order to acquire a magnetic resonance image. In other embodiments, the methods involve administering a sufficient amount of a contrast agent described herein to an animal in order to acquire a magnetic resonance image.

The description of the present invention set forth herein, including the drawings and the examples set forth below, is meant to provide non-limiting description of the compositions and methods of the present invention. It should be apparent that there are variations of the present invention not explicitly presented in this specification that fall within the scope and the spirit of the invention as claimed.

EXAMPLES

Example 1

Mn-12 Clusters

Materials and Methods 4-vinylbenzoic acid (97%), Divinylbenzene (80%), Dichloromethane (anhydrous, 99%), Heptane (anhydrous, 99%), Ethanol (anhydrous, 99%, Toluene (reagent grade), Tetrahydrofuran (anhydrous, 99%), 2,2'-Azobis(2-methylpropionitrile) (98%) and styrene were purchased from Sigma-Aldrich (St. Louis, Mo.). Sodium Dodecyl Sulfate was purchased from Fluka (Seelze, Germany). Hexadecane was purchased from Alfa Aesar (Ward Hills, Mass.). Hydrochloric acid (37%, ACS grade) was purchased from EMD Chemicals (San Diego, Calif.). Polybead® Carboxylate Microspheres (2.73% Solids-Late) were purchased from Polysciences, Inc. (Warrington, Pa.) and separated from water by centrifugation at 4000 RPM for 10 minutes and were allowed to dry overnight. $Mn_{12}O_{12}(O_2CCH_3)_{16}4H_2O$ was synthesized in our lab according to the literature. (T. L is, *Acta Crystallogr. Sect. B*, 1980, 36, 2042).

Fourier Transform Infrared Spectroscopy (FTIR) Characterization

FTIR experiments were recorded in the range 4,000-450 $cm^{-1}$, from pressed pellets in KBr on a Nicolet FTIR. UV-visible spectroscopy was measured from 200-800 nm in ethanol on a HP UV-visible spectrometer in quartz cuvettes. Simultaneous TGA-DTA data were studied from samples in an aluminium pan from 20-1000° C. with a heating rate of 10° C./min. GPC data was obtained at a flow rate of 1 mL/min using a Hewlett Packard series II 1090 Liquid Chromatograph and a Perkin Elmer LC-9S UV/Vis Spectrophotometer as the detector. Samples were prepared for GPC by adding the solid to toluene (4 mL, 2 mg/mL) and mixing with an aqueous solution of HCl (37%, 4 mL). This solution is stirred overnight at room temperature. After the reaction, the two layers are separated and the polystyrene/toluene layer is pumped dry, giving the solid polystyrene, which is then dissolved in THF (1 mg/mL) to make the GPC solutions.

Atomic absorption was measured using a BUCK Scientific Model 200A Atomic Absorption Spectrophotometer. Dynamic Light Scattering was used to calculate particle size. In apparatus used, light from a HeNe laser illuminates dilute suspensions of particles. Light scattered at a fixed angle (usually 90°) is coupled though a narrow band pass optical filter into a single mode optical fiber, which leads to a high sensitivity avalanche photodiode photon counting module (EG&G SPCM-15). The count rates from this detector are analyzed by a hardware autocorrelator (ALV-5000, ALV GmbH, Germany). Using standard assumptions, it can be shown that the decay rate of the count rate autocorrelation function is inversely proportional to the particle diffusion coefficient, from which information on the particle size is obtained. Initial calculations of the particle sizes were determined using a single exponential fit to the autocorrelation functions. AC magnetic measurements were collected on a Quantum Design Physical Measurement System, in zero DC field for temperatures ranging from 1.8-50 K. The AC frequency range was 10-10000 Hz and the amplitude was 1-100e. Experimental data were corrected for sample holder and for diamagnetic contributions calculated from Pascal constants.

Nuclear Magnetic Resonance (NMR) Experiments

Fresh samples for NMR measurements were prepared immediately prior to use. Both the cluster and cluster coated beads were dissolved in distilled water, and filtered via syringe filter. $T_1$ measurements were measured using the inversion recovery pulse sequence, in a field of 300 MHz or 500 MHz, at room temperature with a least squares fit to 10 data points. The $T_2$ was obtained using a conventional spin echo sequence, on a 300 MHz spectrometer and using Carr-Purcell-Meiboom-Gill (CPMG) sequence on 500 MHz Bruker spectrometer. Relaxivity was determined from the slope of a plot of $1/T_1$ or $1/T_2$ versus concentration of Mn-12 and Mn-12 coated beads. The cluster concentration was determined by atomic absorption of Mn.

Concentration Dependent Effect of Mn-12 on $T_1$ and $T_2$

Figure 2:
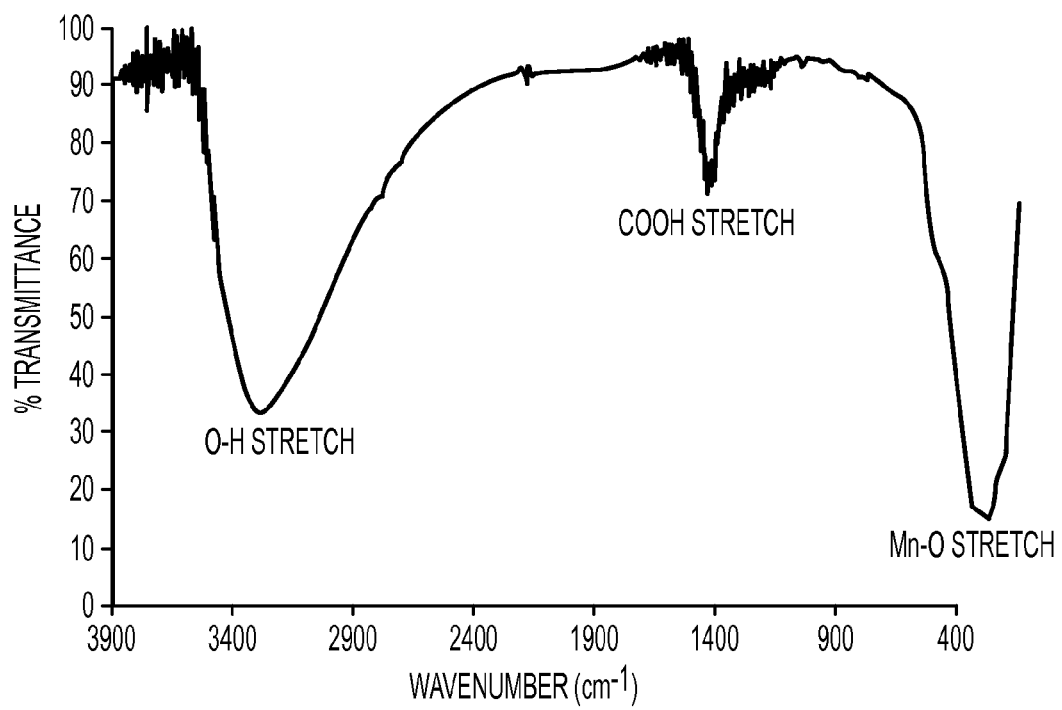
FIG. 2 shows a Fourier Transform Infrared (FTIR) spectrograph of precipitate formed from Mn$_8$O$_{12}$(Ac)$_{16}$ in aqueous solution. Although specific material was determined, the Mn—O, O—H and COOH peaks are clearly visible.

Based on simple criteria, Mn-12 appears ideal as a contrast agent. It has a very high spin-state (high paramagnetic susceptibility), is easily derivatized with a variety of carboxylic acids, and has 4 waters that are intimately associated with the cluster that are exchanged rapidly on the NMR timescale (due to coordination to the labile MnIII) (H. Eppley et al. *J. Am. Chem. Soc,* 1995, 117, 301). However, upon dissolution of Mn-12 in distilled water, within minutes a flocculent material forms. An FTIR of this precipitate is shown in FIG. 2. This poor solubility is a major barrier for potential biomedical applications. However, in the presence of excess carboxylic acid, Mn-12 is stable in aqueous acetic acid solutions and can be re-isolated after many hours.

Figure 3:
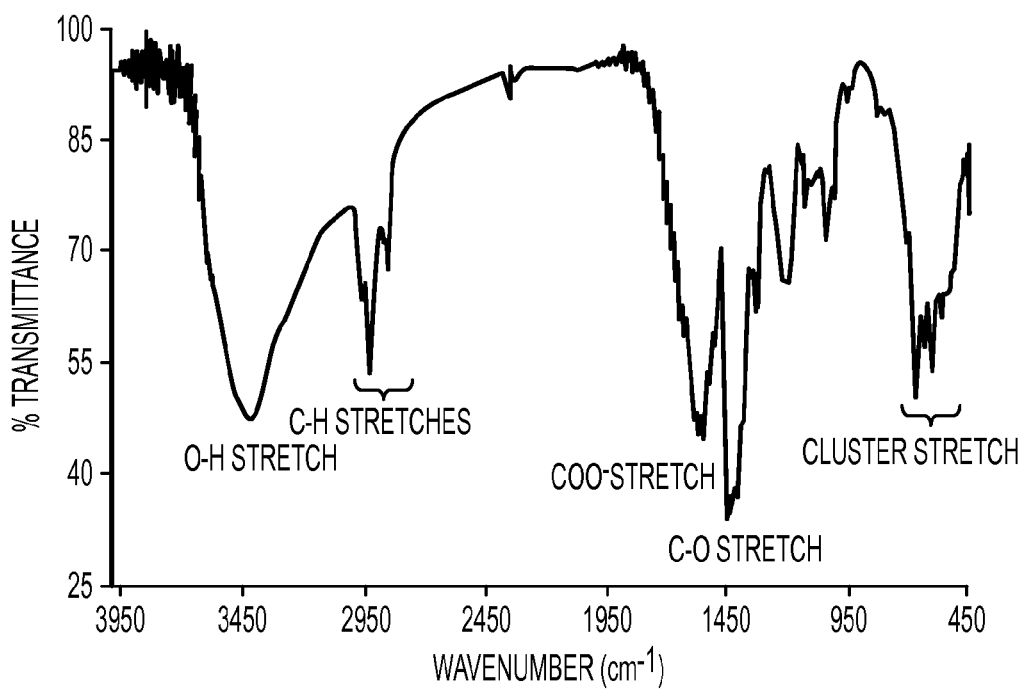
FIG. 3 shows an FTIR spectrograph of Mn-12 re-isolated from acetic acid after soaking for 24 hours. The cluster stretch from 450-700 cm$^{-1}$ is particularly indicative of the intact cluster.
Figure 4:
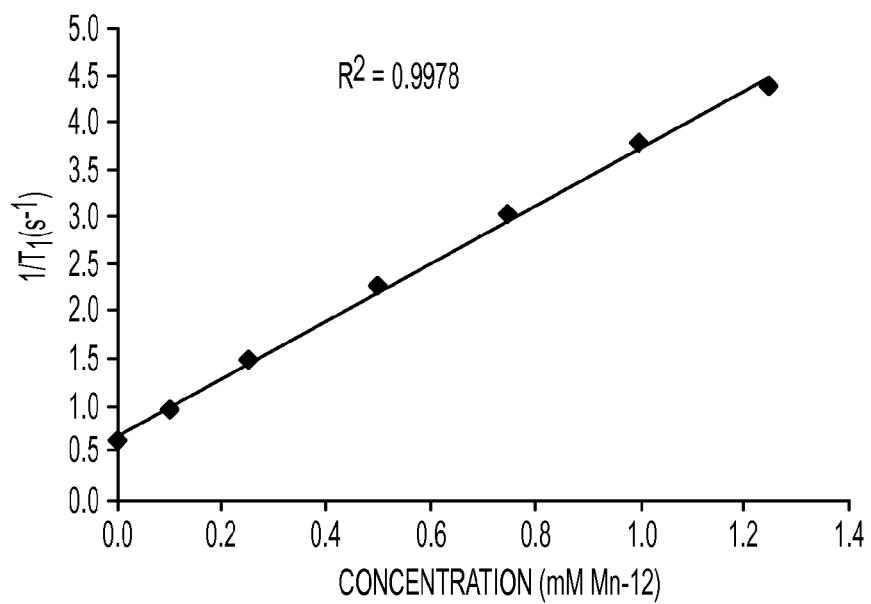
FIG. 4 shows a graph of 1/T$_1$ (s$^{-1}$) versus concentration (mM$^{-1}$) for Mn-12 acetate in D$_2$O and dilute acetic acid.
Figure 5:
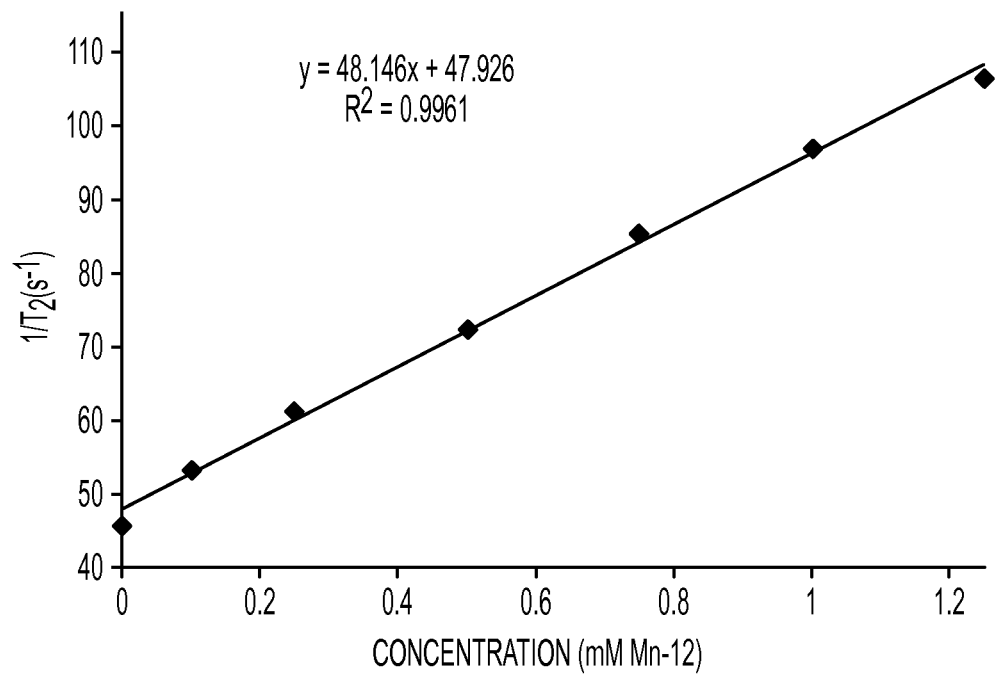
FIG. 5 shows a graph of 1/T$_2$ versus concentration for Mn-12 complex in acetic acid (at 500 MHz).

Taking advantage of this property of Mn-12, the concentration dependent effect of Mn-12 on the $T_1$ and $T_2$ of aqueous protons in acetic acid solutions was studied. The cluster was identified by FTIR (FIG. 3) after each NMR experiment to confirm the structural integrity, although below 0.5 mM the amount of material recovered was so small definitive spectroscopic characterization was difficult. A graph of $1/T_1$ versus concentration (FIG. 4) was linear with $R^2=0.9978$ and gave an $r_1$ of $3.0\pm0.1$ $mM^{-1}V$. The analogous graph for $1/T2$ (FIG. 5), had an $R^2=0.9961$ and gave $r_2=48\pm1$ $mM^{-1}s^{-1}$. For comparison of our S=10 molecule to gadolinium S=7/2 molecules, relaxivity values are reported in $mM^{-1}$ of the cluster (as opposed to $mM^{-1}$ of metal). Gadolinium complexes typically have $r_1$ values that range from 4-16 depending on the ligands, (S. Aime et al. *J. Magn. Res. Imaging,* 2002, 16, 394) while iron oxide nanoparticles are generally found to be ~30 $mM^{-1}s^{-1}$ ($r_2$~100 $mM^{-1}s^{-1}$) (Y.-X. J. Wang et al., *Eur. Radiol.,* 2001, 11, 2319). Interestingly the $r_2/r_1$ values for iron oxide tend to range from 40-100, resulting in a $T_2$ weighted contrast agent. Here the Mn-12 clusters appear to be intermediate, somewhat closer to Gd complexes, with a $r_1/r_2$ of 16.

The experiments reported here were predominantly done at much higher fields (300-500 MHz), than normally used for MRI, and the temperatures were almost all room temperature. The relaxivity of Mn-12 at 37° C. was measured, and it was found that the relaxivity decreased at higher temperatures, similar to molecules for which the rotational correlation time is a factor (K. Raymond et al., *Bioconjugate Chem.* 2005, 16, 3). Although a thorough study of the field dependence of the relaxivity has not been done, measurements at 300, 400, and 500 MHz show that the relaxivity appears to increase with higher fields, similar to the Gd—HOPO complexes and unlike commercially available contrast agents (K. Raymond et al., *Bioconjugate Chem.* 2005, 16, 3). This may be an advantage as the fields used for MRI have been increasing, placing new demands on contrast agents D. Fulton et al., *Chem. Commun.* 2006, 1064.

Synthesis of Mn-12 Coated Polystyrene Beads

It has been previously demonstrated that Mn-12 can undergo ligand exchange for attachment onto any surface containing carboxylic acid functionality (Steckel et al., *Nano Lett.,* 2004, 4, 399). With multiple sites of attachment, the chelate effect stabilizes the cluster on surfaces even under a flow of fresh solvent as demonstrated by quartz crystal microbalance studies of carboxylate terminated SAMs with a monolayer of Mn-12 attached. As described herein, using a similar ligand exchange method, it is possible to attach the cluster to a polystyrene bead with a carboxylate surface, forming a water soluble, stable bead as illustrated in FIG. 1.

The Mn-12 coated polystyrene beads were synthesized as follows. Dry polystyrene beads were suspended in dry ethanol and soaked for 24 hours prior to surface attachment. A solution of $Mn_{12}O_{12}(O_2CCH_3)_{16}$ in ethanol (2 mM) was filtered and added to the ethanolic solution of beads and this mixture was stirred for 2 hours. The Mn-12 coated beads were removed from solution by centrifugation at 4000 RPM for 10 minutes. The beads were washed with ethanol and centrifuged and isolated 3 times. The FTIR of the beads matched that of polystyrene. Based on monolayer coverage (assuming 177 ng/cm² from QCM data of thin films), the theoretical [Mn] for 47 nm, 120 nm, 209 nm, 489 nm, 994 nm beads were 7.0%, 3.1%, 1.9% and 0.83% and based on atomic absorption the [Mn] was 1.7%, 2.3%, 0.5% and 0.2% respectively. The actual concentration of Mn by atomic absorption was used in determining the relaxivity reported. These were reproducible. The beads coated with Mn-12 can be dissolved in water, and after 48 hours the supernatant shows no evidence of manganese by atomic absorption experiments.

Figure 6:
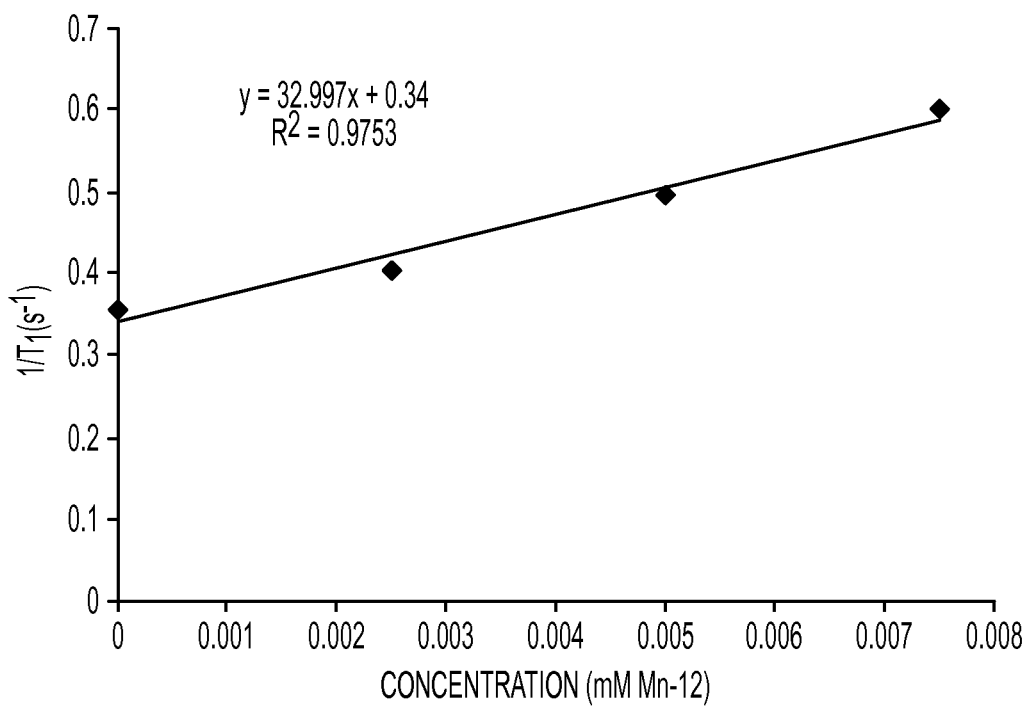
FIG. 6 shows a graph of 1/T$_1$ versus concentration for 209 nm Mn-12 coated beads (at 300 MHz).
Figure 7:
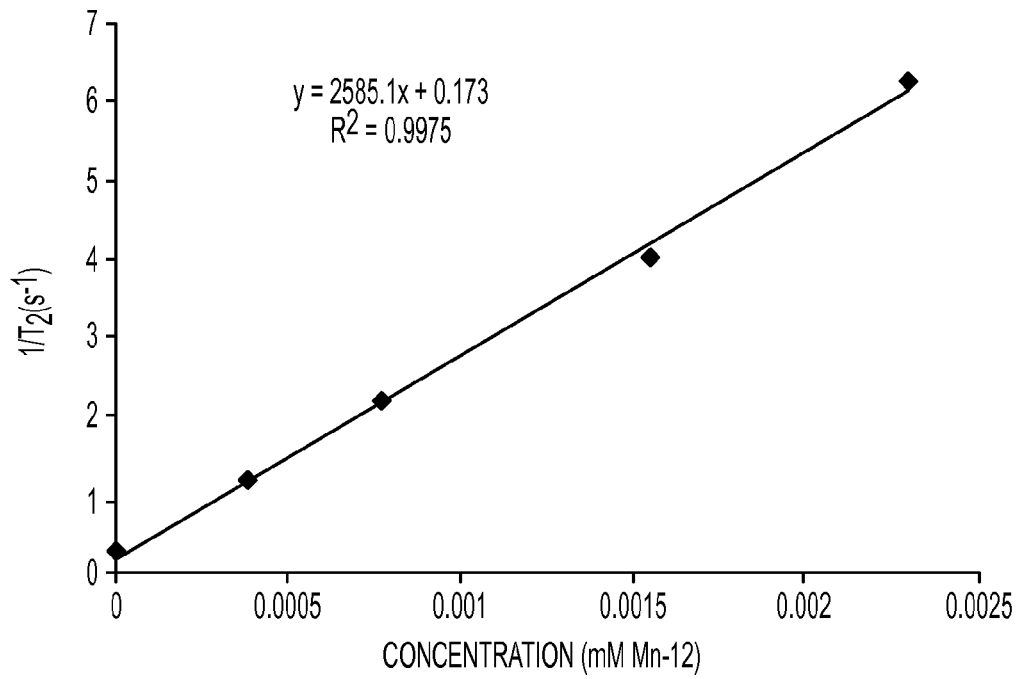
FIG. 7 shows a graph of 1/T$_2$ versus concentration for 209 nm Mn-12 coated beads (at 300 MHz).

Plots of $1/T_1$ and $1/T_2$ versus concentration for 209 nm beads are shown in FIGS. 6 and 7, respectively. The relaxivity of cluster coated 200 nm beads is included in Table 1. The n per molecule increased to 37.5±4.5 mM$^{-1}$s$^{-1}$. The Solomon-Bloembergen-Morgan theory (N. Bloembergen et al., *Phys. Rev.* 1948, 73(7), 679; N. Bloembergen et al, *J. Chem. Phys.* 1961, 34(3), 842; I. Solomon, *Phys. Rev.* 1955, 99(2), 559) predicts that the inner sphere relaxivity should be dominantly influenced by the reorientational correlation time ($\tau_R$). In essence, longer $\tau_R$ or slower tumbling agents should have faster relaxation rates and higher relaxivities (E. Weiner et al., *J. Am. Chem. Soc.* 1996, 118, 7774; M. Bottrill et al., *Chem. Soc. Rev.* 2006, 35, 557). Although the reorientational correlation time has been associated with molecular weight, shape is also important, and the effect can be enhanced for spherical agents (M. Lowe, *Aust. J. Chem.* 2002, 55, 551; P. Caravan, *Chem. Soc. Rev.*, 2006, 35, 512). For example, multimeric gadolinum complexes in modified dextran polymers the per gadolinium relaxivity $r_1$ increases to 10.6 mM$^{-1}$s$^{-1}$ (C. Casali et al., *Acad. Radiol.* 1998, 5, S214). Other macromolecular gadolinium complexes, such as polyamide dendrimers, also exhibit an increased $r_1$ (~16.5 mM$^{-1}$sec$^{-1}$ per gadolinium) (M. Rohrer et al., *Invest. Radiol.* 2005, 40, 715).

TABLE 1

Relaxivity of Clusters and Cluster Coated Beads

| Sample | $r_1$ | $r_2$ | $r_2/r_1$ |
|---|---|---|---|
| $Mn_{12}O_{12}Ac_{16}$ RT [a] | 3.0 ± 0.1 | 48 ± 1 | 16 |
| $Mn_{12}O_{12}Ac_{16}$ (37° C.) [a] | 2.7 ± 0.1 | 34 ± 1 | 13 |
| $Mn_{12}O_{12}$—OOC-Bead (RT) [b] | 37.5 ± 4.5 | 2585 ± 74 | 69 |

[a] experiment in $D_2O$ and dilute acetic acid (500 MHz)
[b] in $D_2O$, 209 ± 11 nm bead (300 MHz).

Effect of Bead Diameter on $r_1$

Figure 8:
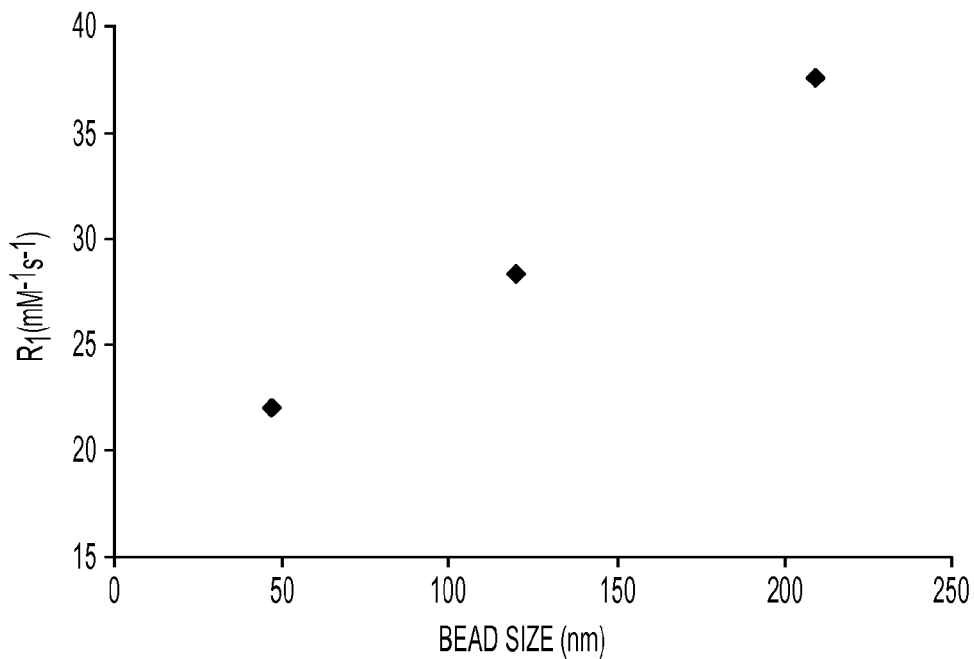
FIG. 8 shows a plot of the per cluster r$_1$ (mM$^{-1}$s$^{-1}$) versus bead diameter (nm).

To determine whether the reorientational correlation time is important in this system the effect of bead diameter on n was investigated. As the bead diameter was increased from 47.1±1.5 nm to 209±11 nm, the per cluster $r_1$ increased from 22.0±2.5 s$^{-1}$ to 37.5±4.5 s$^{-1}$ as shown in FIG. 8.

Figure 9:
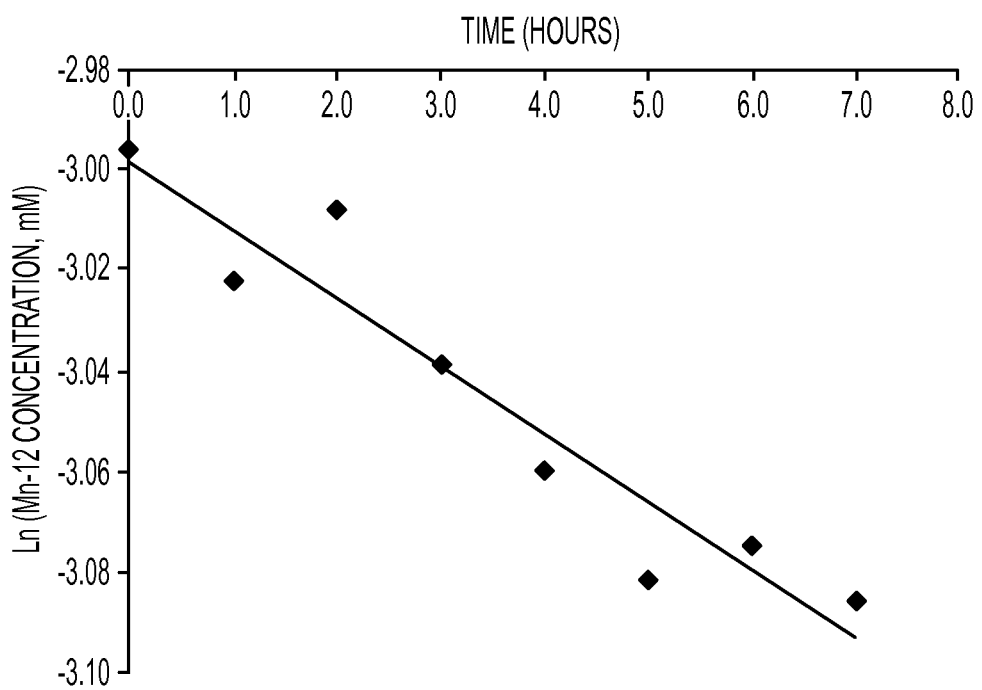
FIG. 9 shows a plot of Ln[intact Mn-12] as a function of time for Mn-12 coated 209 nm beads.

The relative stability of Mn-12 in neutral aqueous solutions upon surface attachment was also studied. It was found that the $T_1$ slowly increased (i.e. the relaxivity decreased) over a 10 hour period. Solutions of cluster coated beads that have soaked over night exhibit no precipitate and do not release manganese into the solution. Therefore gradual decrease in n over time for Mn-12 coated beads, must be a result of a reduction of the spin state possibly due to structural changes to the surface attached cluster. Assuming that the relaxivity of the cluster is a constant, the changes in $T_1$ were used to calculate the change in concentration of intact cluster. This assumes that whatever form of manganese oxide is left on the surface is inactive towards relaxivity. A plot of ln[Intact Mn-12] as a function of time followed first order kinetics (FIG. 9) with a rate constant k=0.013 hr$^{-1}$, and a half life of 51 hours.

Formation of Co-polymers of Substituted Mn-12 Clusters and Styrene

To enhance the stability of the cluster further, an alternative of forming co-polymers of styrene with substituted Mn-12 clusters was investigated. Using 'miniemulsions', polymerization of droplets with a size range of 50-500 nm (K. Landfester, *Annu. Rev. Mater. Res.* 2006, 36, 231; K. Landfester et al., *Macromolecules,* 1999, 32, 5222), stable, homogenous, magnetic co-polymer nanobeads were formed. Ligand substitution of acetate for a polymerizable carboxylic acid such as methacrylic acid results in a cluster with functionality for olefin polymerization. The reaction with styrene, emphasizing the polymerization chemistry is shown in Scheme I, where $L=O_2CH=CH=R$.

Scheme I

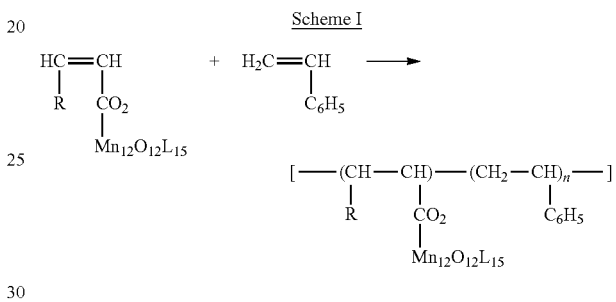

Similar bulk co-polymers have been reported for methacrylic acid substituted clusters polymerized with methyl methacrylate which resulted in materials with enhanced chemical stability towards water and heat (S. Willemin et al., *New. J. Chem.* 2004, 28, 919; F. Palcio et al., *J. Mater. Chem.* 2004, 14, 1873). Synthesis of a substituted cluster with L=vinyl benzoic acid is reported for the first time herein. The vinyl benzoic acid may be co-polymerized with styrene. The initial choice of styrene as the co-monomer was based on biostability, and the fact that styreneis inexpensive and easily surface functionalized to control solubility and the binding of antibodies or proteins (K. Landfester et al., *J. Phys: Condensed Matter,* 2003, 15, S1345) as well as based on previous experience forming monodispersed nanobeads of polystyrene (E. Van Keuren, *J. of Dispersion Sci. and Tech.* 2004, 25(4), 1). Vinyl benzoic acid was chosen as the substituent ligand due to its similarity to styrene.

Mn-12 vinyl benzoic acid monomers (Mn-12-VBA) was prepared as follows. The preparation of Mn12-VBA was based on a method described elsewhere (a) E. Weiner et al., *J. Am. Chem. Soc.* 1996, 118, 7774; M. Bottrill et al., *Chem. Soc. Rev.*

2006, 35, 557). Briefly, 4-vinylbenzoic acid (1.5 mmol) was added to a slurry of $Mn_{12}O_{12}(O_2CCH_3)_{16}$ (0.0625 mmol) in dichloromethane (25 mL). The solution was stirred for 4 hours, filtered to a beaker and layered with heptanes (50 mL). A brown solid precipitate formed after approximately 24 hours. The procedure was repealed to ensure complete exchange of vinylbenzoic acid for acetate to yield a final product $Mn_{12}O_{12}(OOCC_6H_4CH=CH_2)_{16}(H_2O)_4$. IR (KBr cm$^{-1}$): 3401 (m, br), 3082 (w), 3066 (w), 3006 (w), 2923 (w), 1929 (w), 1835 (w), 1700 (m), 1624 (w), 1606 (s), 1578 (s), 1507 (s), 1410 (vs), 1347 (s), 1289 (m), 1183 (s), 1110(m), 1016 (s), 988 (m), 914(m), 862 (s), 790 (s), 771 (m), 718 (s), 663 (m), 625 (s), 552 (m), 518 (s). UV-visible $1_{max}$ acctonitrile nm ($\epsilon Mn, L^{-1}cm^{-1}$): 510 nm (580), 747 nm (108). Anal. Calc. (Found) for $C_{153}H_{130}O_{51}Mn_{12}$: C, 52.77 (52.31); H, 3.70 (3.95). Percent yield 91.90%.

Before synthesizing and studying the co-polymers the magnetic properties of this new Mn-oxo cluster were investigated, $Mn_{12}O_{12}(O_2C-C_6H_4-CH=CH_2)_{16}$ ([$Mn_{12}O_{12}VBA_{16}$]) because it has not been reported previously. As described below, the magnetic properties are generally consistent with Mn-12 with acetate ligands. The ground state of the cluster has been determined using the in-phase molar AC susceptibility $\chi^{-1}$ measurements. From the plateau in the $\chi'T$ versus T plot, an effective moment μeff for [$Mn_{12}O_{12}VBA_{16}$] is found at 19.1 μB with spin S=9.1, compared with μeff=17.4 μB and spin S=9 for [$Mn_{12}O_{12}Ac_{16}$] (E. Weiner et al., *J. Am. Chem. Soc.* 1996, 118, 7774; M. Bottrill et al., *Chem. Soc. Rev.* 2006, 35, 557). The Weiss temperature, Θ/K=3.9, and the Curie constant was C=31.3 were based on analysis of the Curie plot.

Figure 10:
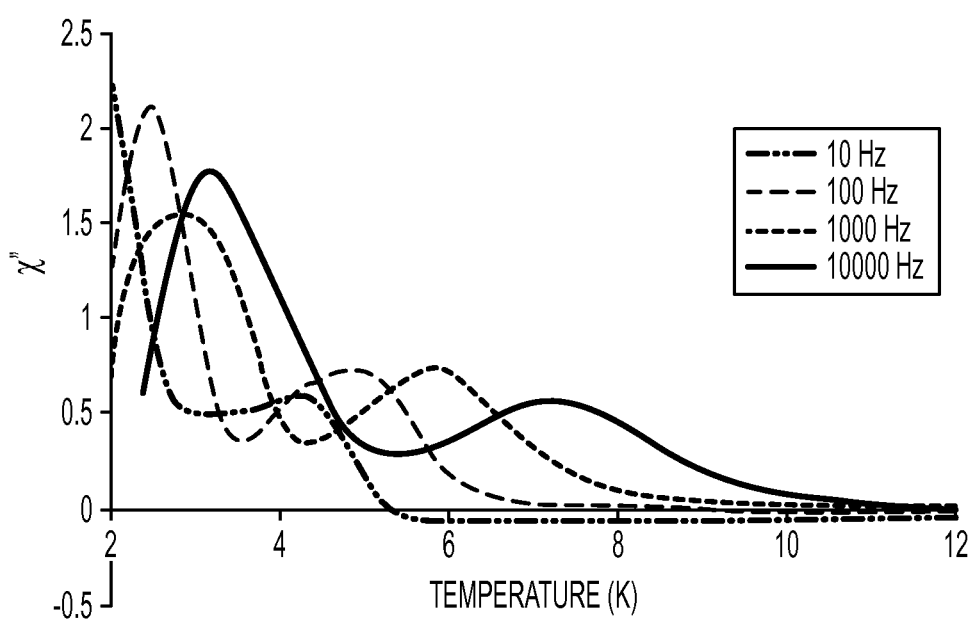
FIG. 10 shows a plot of the AC susceptibility χ"-versus-temperature for [Mn$_{12}$O$_{12}$(VBA)$_{16}$].

One of the most striking features of 'Single Molecule Magnets' is the temperature dependence of the out-of-phase AC susceptibility signal ($\chi''$). The peak corresponds to the temperature at which the rate of the flip of the molecular moment is equal to the AC frequency, v' (E. Weiner et al., *J. Am. Chem. Soc.* 1996, 118, 7774; M. Bottrill et al., *Chem. Soc. Rev.* 2006, 35, 557). The appearance of two maxima in $\chi''$ as a function of temperature at 2.2 and 4.4K at 10 Hz (see FIG. 10) suggests two relaxation mechanisms.

Figure 11:
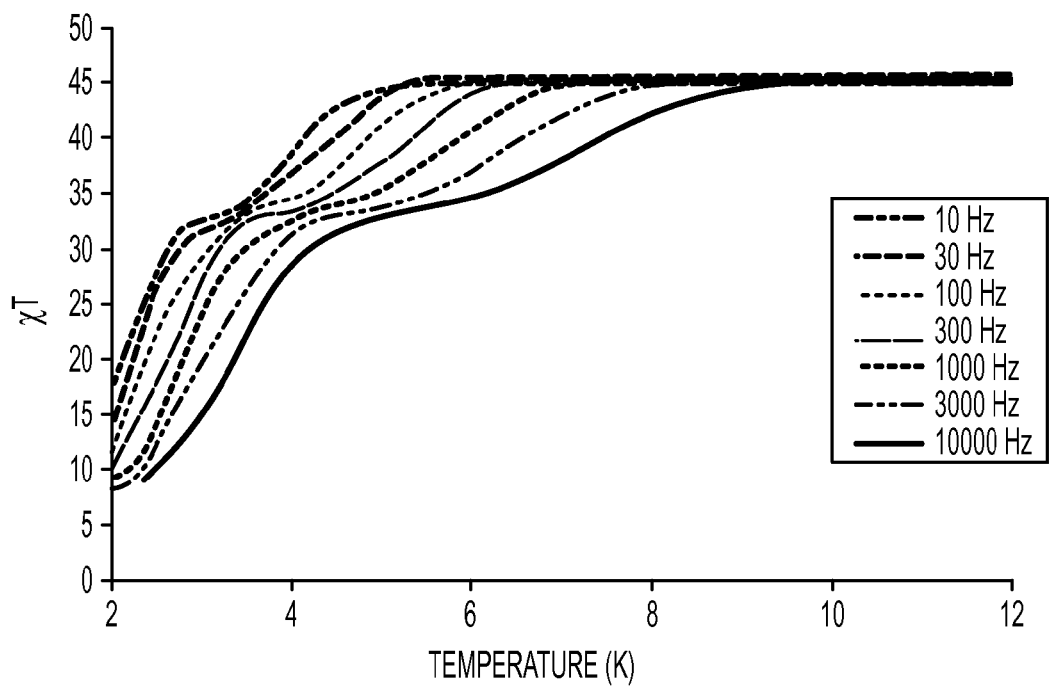
FIG. 11 shows a plot of χ'T-versus-Temperature (K) for [Mn$_{12}$O$_{12}$(VBA)$_{16}$].
Figure 12:
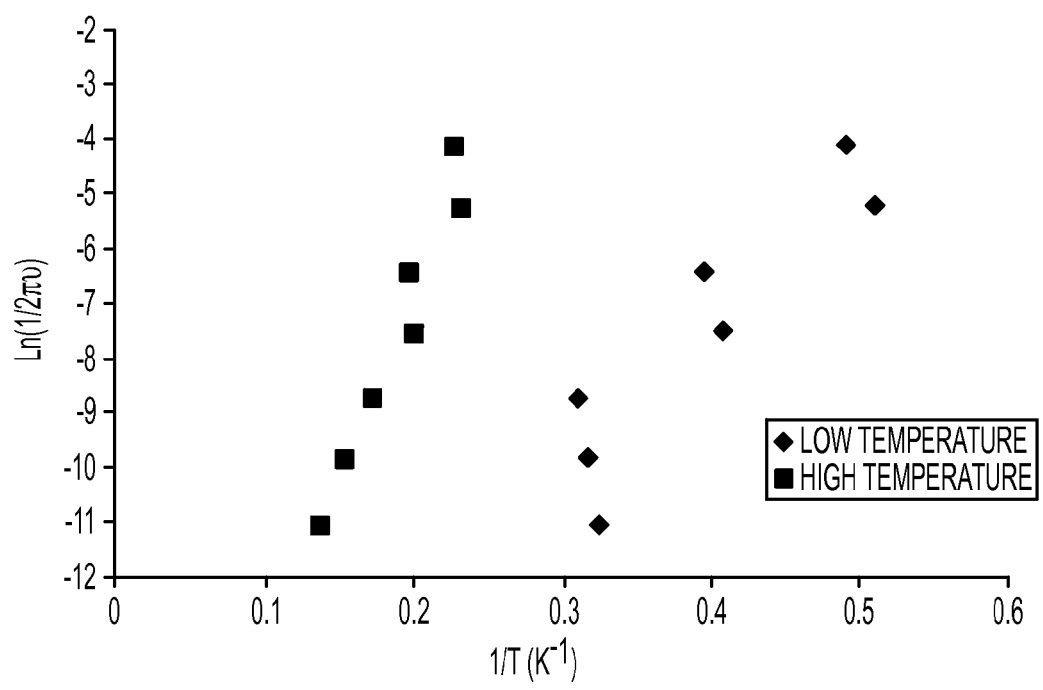
FIG. 12 shows an Arrhenius Plot for [Mn$_{12}$O$_{12}$(VBA)$_{16}$].

Several complexes with composition [$Mn_{12}O_{12}(O_2CR)_{16}$] exhibit two out-of phase AC magnetic susceptibility signals, typically in the 4-7K and 2-3K region. The presence of two relaxation mechanisms has been attributed to the presence of two isomers of the complex, either in the placement of the four $H_2O$ ligands or Jahn-Teller isomerism (S. Aubin et al., *Inorg. Chem.* 2001, 40, 2127). Likewise, as shown in FIG. 11, there are two plateaus in the $\chi'T$ vs T, consistent with two relaxation mechanisms. The shift to lower temperature as the frequency decreases in the $\chi''$ as a function off, is typically seen in Mn-12 clusters (H. Eppley et al., *J. Am. Chem. Soc,* 1995, 117, 301). As shown in FIG. 12, using an Arrhenius plot of $1/v^{-1}$ versus the peak temperature (where $v^{-1}$ is the AC frequency) the energy barrier to spin reversal. U/K was determined to be 65.9 with a relaxation time, τ0=4.22×10$^{-8}$ s$^{-1}$ (high temperature peak) and U/K=27.4 with a of 1.04×10$^{-8}$s$^{-1}$ (low temperature peak). This is comparable to the high temperature peak with U/K=61 and τ=2.1×10$^{-7}$ s$^{-1}$ for [$Mn_{12}O_{12}Ac_{16}$](R. Sessoli et al., *Nature,* 1993, 365, 141; D. Gatteschi et al., *Science* 1994, 265, 1054).

Figure 13:
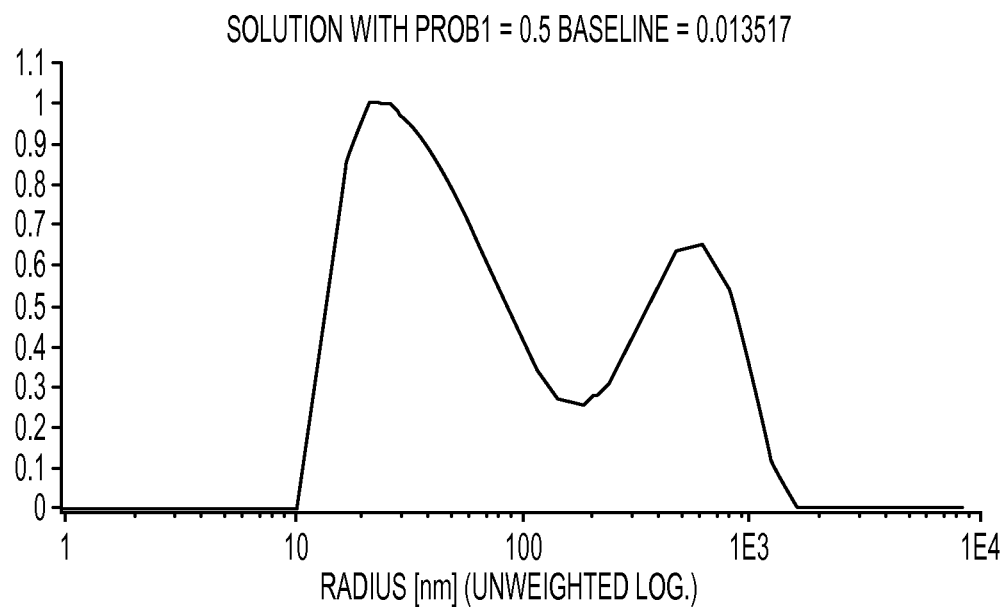
FIG. 13 shows the dynamic light scattering of co-polymer beads.
Figure 14:
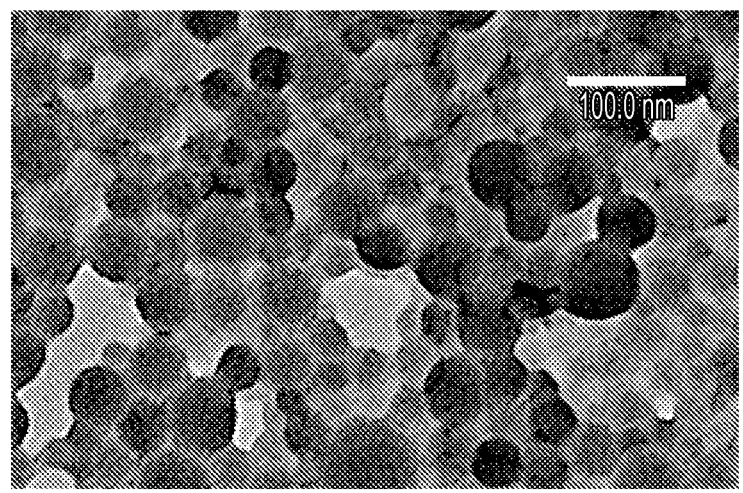
FIG. 14 shows a scanning electron micrograph of co-polymer beads.

For co-polymerization, miniemulsions were prepared from [$Mn_{12}O_{12}VBA_{16}$], styrene, 1% divinylbenzene (DVB), the hydrophobe hexadecane in aqueous solutions of SDS using AIBN as an initiator. For pure polystyrene miniemulsions, the hydrodynamic diameter of the beads formed is generally determined by the ultrasonication time, polymerization initiation time after sonification, as well as surfactant concentration (K. Landfester et al., *Macromolecules,* 1999, 32, 5222). Our preliminary experiments used ultrasonification times and surfactant concentrations associated with 100 nm polystyrene beads. However, analysis of dynamic light scattering (DLS) experiments (FIG. 13) indicated that the median radius of the beads were 1 μm, and SEM images (FIG. 14) suggest agglomeration of smaller particles. It is likely that the Mn-12 and DVB affect the solubility, so the amount of surfactant was increased significantly resulting in beads with much smaller diameters. There appeared to be two main components to the particle size distribution at 40 nm and ~1 μm in diameter from the DLS.

Figure 15:
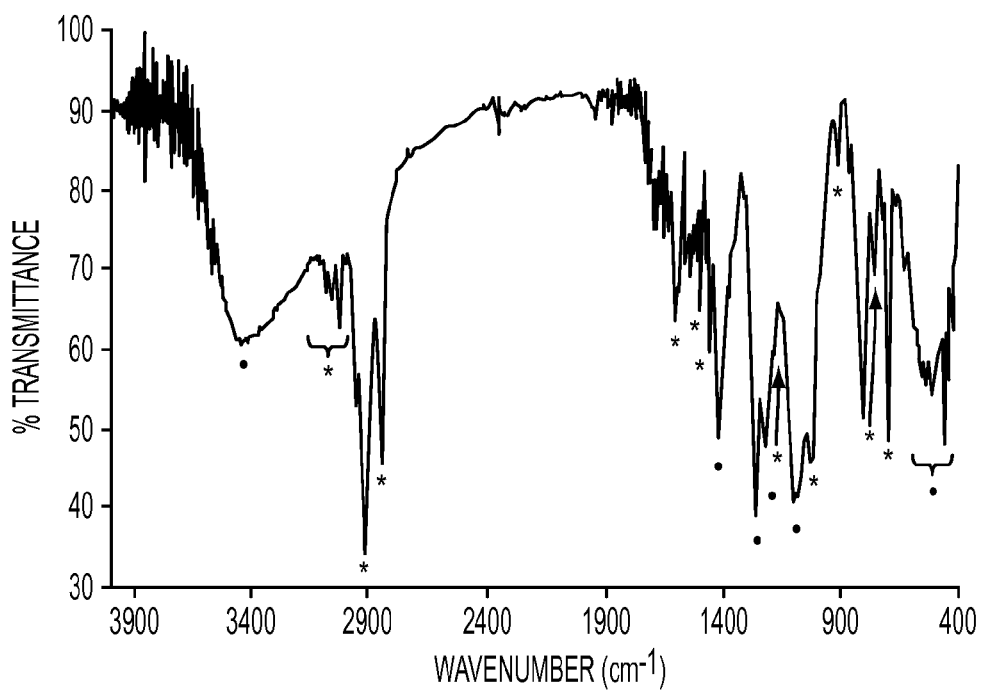
FIG. 15 shows an FTIR spectrograph of co-polymer beads. * indicates peaks that match that of polystyrene; • indicates peaks that match that of Mn$_{12}$O$_{12}$VBA$_{16}$.
Figure 16:
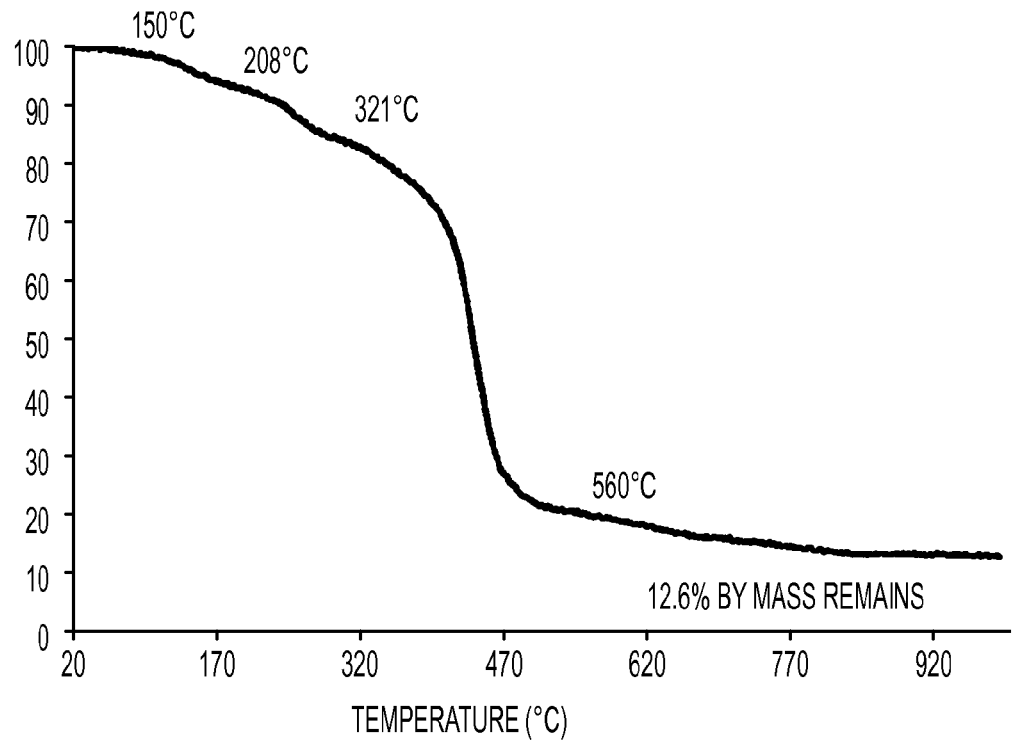
FIG. 16 shows a plot of a thermogravimetric analysis of co-polymer beads. 9.6% by weight remains at 1000° C., which is Mn$_3$O$_4$ as shown by powder diffraction.
Figure 17:
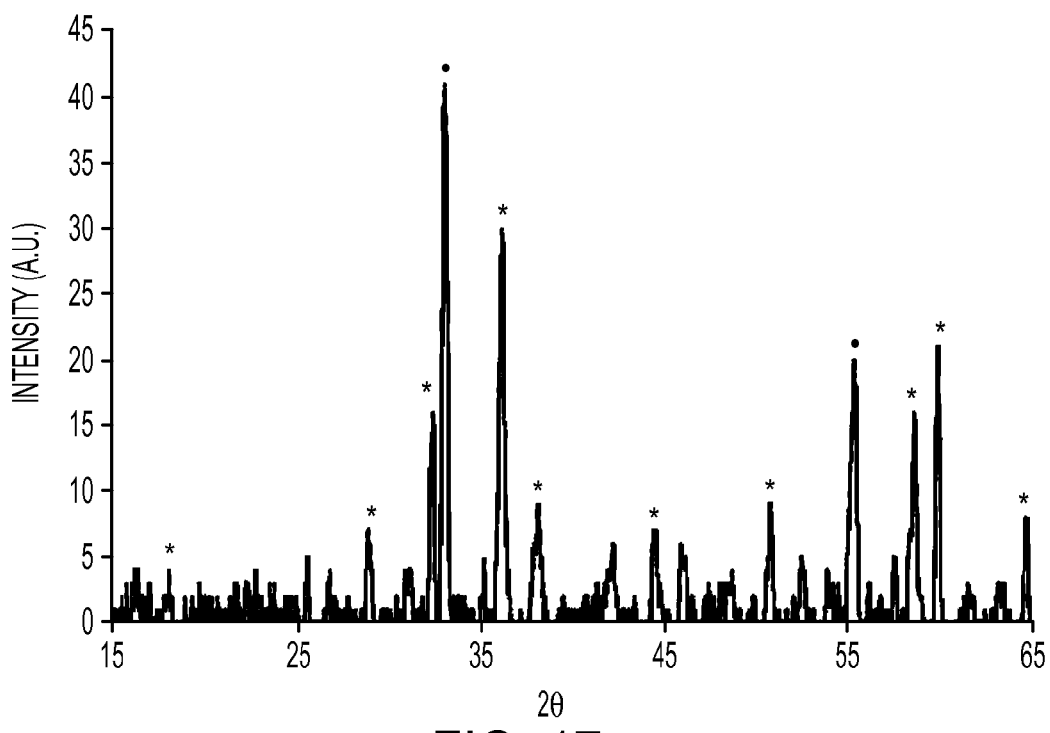
FIG. 17 shows the x-ray powder diffraction spectra of material remaining after thermogravimetric analysis of copolymer beads. * indicates peaks that index to $Mn_3O_4$ and • indicates peaks that index to $Mn_2O_3$.

Miniemulsion polymerization was performed as follows. The substituted cluster, $Mn_{12}O_{12}(OOCC_6H_4CH=CH_2)_{16}$ $(H_2O)_4$ (0.0345 mmol), styrene (6.78 mmol) and divinylbenzene (1 wt %) were combined first to form the oil phase. To this solution, both 2,2'-Azobisisobutyronitrile (0.24 mmol) and hexadecane (0.13 mmol) were added, stirred and degassed. A second solution, containing sodium dodecyl sulfate (0.28 mmol) dissolved in distilled $H_2O$ (8 mL) forming the aqueous phase, was degassed then combined with the Mn-12/styrene solution. The resulting mixture was then placed in an ultrasound (Fisher 550 Sonic Dismembrator) at a setting of 5 for 90 seconds. Finally, the mixture was placed in a water bath at 60° C. (New Brunswick Scientific C76 Water Bath Shaker) for 6 hours. The solution was immediately removed from the water bath and the Mn-12/polystyrene beads were removed from solution by centrifugation at 4000 RPM. The beads were washed with ethanol, and dried. The manganese content based on atomic absorption was 0.82%, compared with the theoretical amount (assuming a 1:200 ratio of cluster to styrene) of 2.73%. Gel permeation chromatography of the organic fraction gave a broad peak at 15 minutes, which corresponded to the average molecular weight of 6217 g/mol. FIG. 15—FTIR (KBr, cm$^{-1}$): 3444 (m, br), 3082 (w), 3061 (w), 3026 (w), 2958 (m), 2920 (s), 2850 (s), 1940 (w), 1600 (m), 1581 (w), 1492 (m), 1454 (m), 1412 (s), 1261 (s), 1217 (s), 1182 (m), 1095 (s), 1026 (m), 908 (m), 862 (w), 802 (s), 758 (m), 698 (vs), 626 (w), 534 (m), 503 (m), 457 (m). As shown in FIG. 16, thermogravimetric analysis of the beads exhibited three steps in the thermal decomposition at 128° C., 227° C. and 397° C., leaving 9.6% of the mass. As shown in FIG. 17, the X-ray powder diffraction pattern of the residue matched that of $Mn_3O_4$, d (hkl); 4.92 (101), 3.08 (112), 2.88 (200), 2.76 (103), 2.49 (211), 2.04 (220), 1.70 (312), 1.64 (303), 1.54 (224), 1.44 (314).

Unlike miniemulsions of pure polystyrene, which polymerize between 10 mins-2 hours depending on the conditions, the copolymer reactions were left for ~6 hours. At shorter periods, it was possible to smell styrene and no powder was obtained. After 6 hours, the FTIR of the isolated product matches that of polystyrene. The intensity of the C=C bands at 1630 cm-1 were lost, suggesting complete polymerization. Unfortunately the peaks unique to the cluster (particularly the core stretches between 450-650 cm-1) are obscured by die strong polymer peaks.

Figure 18:
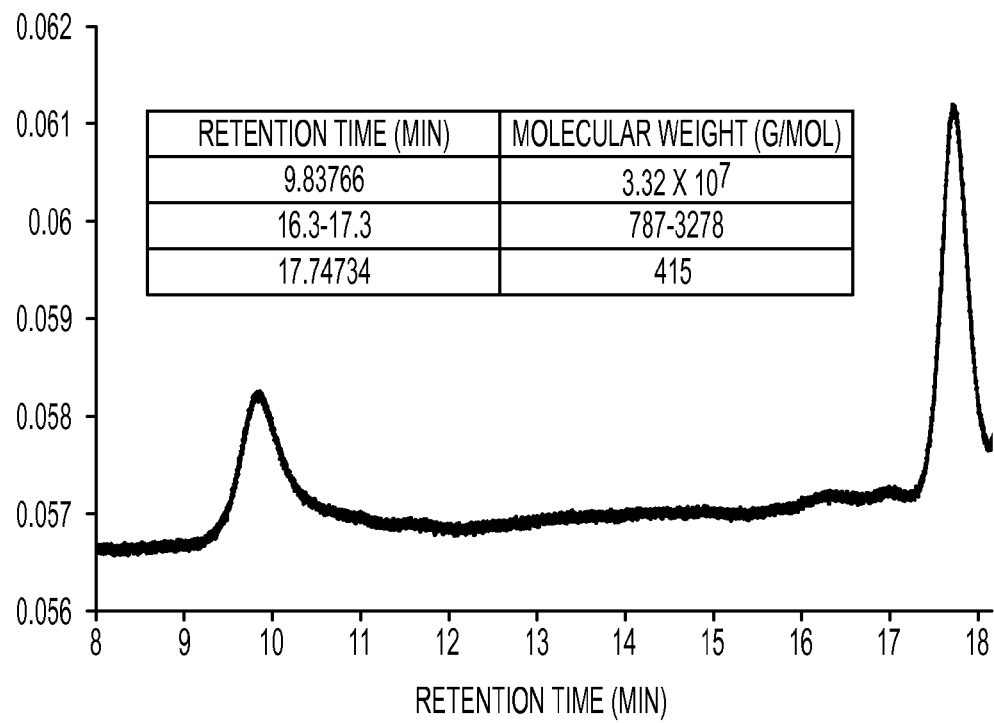
FIG. 18 shows a chromatogram of gel permeation chromatography performed on co-polymer beads.

As seen previously in the literature for bulk co-polymers, the TGA data (FIG. 16) showed that the co-polymer beads decompose in one step, at higher temperatures (here by 7° C.) than pure polymer, and the residue has an X-ray powder diffraction pattern that indexes to $Mn_3O_4$ (FIG. 17). The washed and dried co-polymer was separated into its organic and inorganic components with an acid-toluene solvent mixture. As shown in FIG. 18, the isolated organic polymer was then characterized by gel permeation chromotography (GPC). The GPC indicated the average molecular weight was 6217 g/mole, which corresponded to ~60 styrene units, quite low compared with miniemulsion reactions of pure polystyrene (with molecular weights as high as 105). The manganese content of the inorganic component, based on atomic absorption suggested a metal molar percent of 0.82% Mn. Interestingly, this was higher than expected for the reactant stoichiometry which would give 0.5% (for stoichiometric ratio of 1:200).

Figure 19:
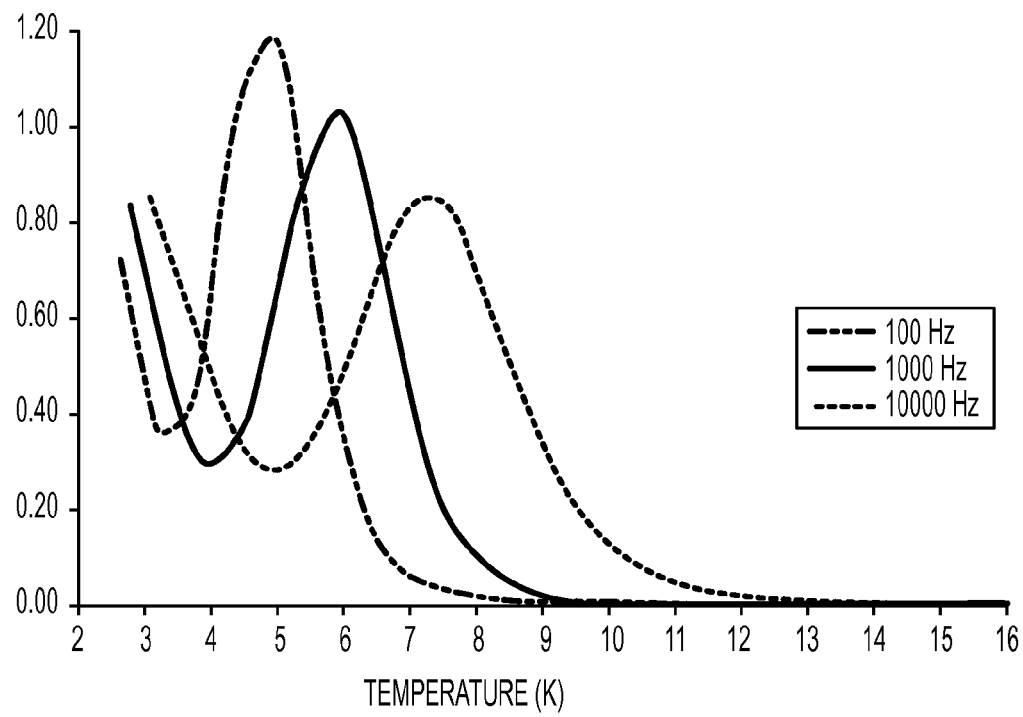
FIG. 19 shows a plot of the AC susceptibility $\chi''$-versus-temperature for co-polymer.

The AC susceptibility measurements indicate the spin state of the metal was 6, lower than that found for the unpolymerized cluster. This is consistent with bulk measurements of the copolymer where Mn-12 is substituted with acrylate, $Mn_{12}O_{12}(Acrylate)_{16}$, and polymerized with ethyl acrylate under similar conditions (S. Willemin et al. *New J. Chem.*, 2004, 28, 919.) The other example of an Mn-12 copolymer, Mn12O12(Methaerylate)16 with methyl-methacrylate did not report the $1/\chi'$ versus temperature or the spin state (F. Palacio et al. *J. Mater. Chem.* 2004, 14, 1873.) Interestingly, a peak in $\chi''$ versus temperature was observed, as show in FIG. 19. (S. Willemin et al. *New J. Chem.*, 2004, 28, 919; F. Palacio et al. *J. Mater. Chem.* 2004, 14, 1873.)

The spin state was calculated to be only S=5, much lower than expected. The energy barrier for the two peaks were 64.8 (U/K) and $\tau_0=1.29\times10^{-9}$ Hz for the high temperature peak, and 19.6 (U/K) and $\tau_0=3.99\times10-8$ Hz for the low temperature peak.

Preliminary relaxivity measurements were done, and an estimate of $r_1$ was 23.6±2.5 mM-1s-1. However it is noted that there was a wide distribution of particle sizes in the described synthesis, and as has been demonstrated here, there is a strong dependence of relaxivity on bead diameter.

Example 2

Mn—Fe-oxo Clusters

General Information

All chemicals and solvents were obtained from Sigma-Aldrich and used as received. Infrared spectra were measured in the range 450-4000 cm$^{-1}$ as pressed KBr pellets on a Nicolet 380 FTIR spectrometer. Elemental analysis was performed on a Perkin Elmer 2400 Elemental Analyzer, using acetanilide as standard. X-ray powder diffraction patterns were obtained using a Rigaku RAPID Curved IP X-ray powder diffiactometer with Cu Kα radiation and an image plate detector.

Figure 20:
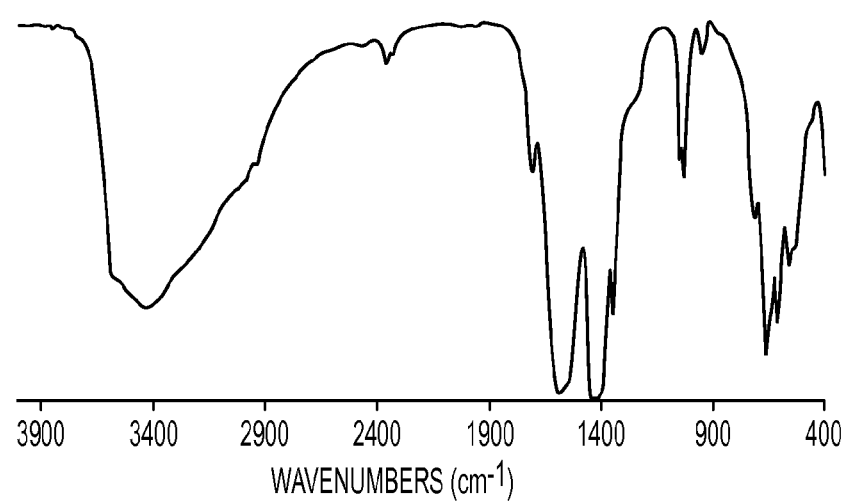
FIG. 20 shows an FTIR spectrograph of $Mn_8Fe_4$ as prepared in Example 2.
Figure 21:
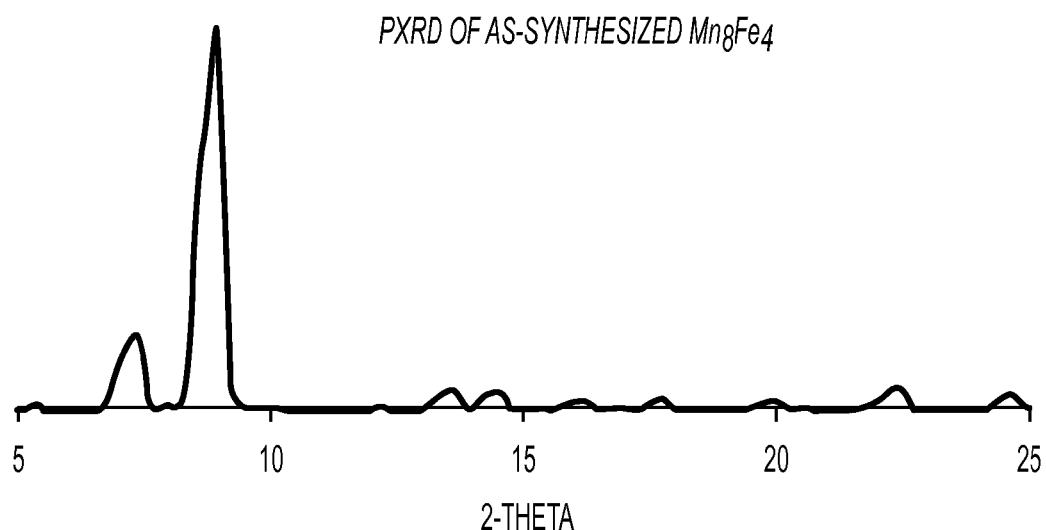
FIG. 21 shows the powder X-ray diffraction data, both actual and calculated, for $Mn_8Fe_4$.
Figure 21:
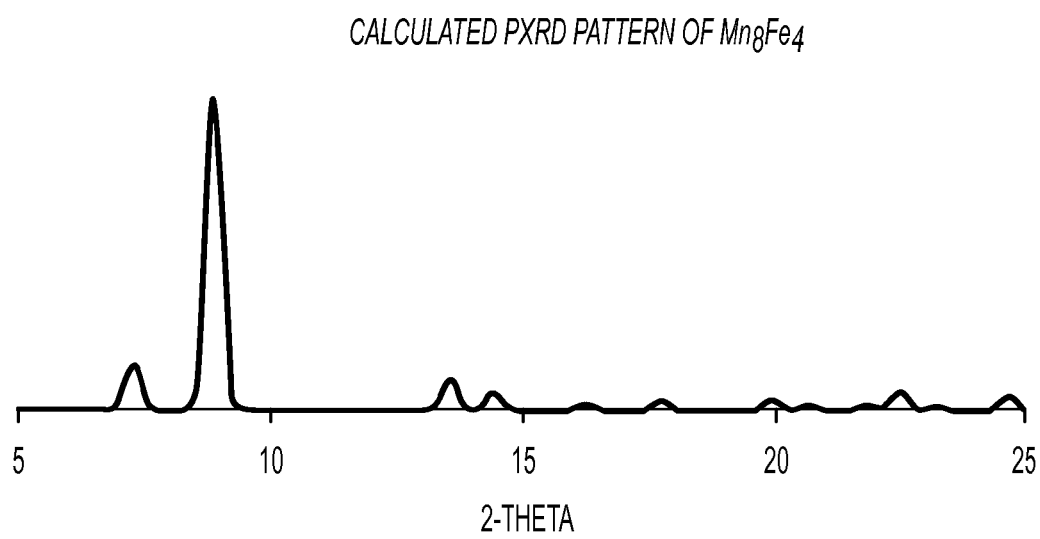

Synthesis of $Mn_8Fe_4$ $[Mn_8Fe_4O_{12}(O_2CCH_3)_{16}(H_2O)_4]\cdot 4H_2O\cdot 2CH_3COOH$, denoted here as $Mn_8Fe_4$, was prepared as described in previous reports (A. R. Schake, et al., *Inorg Chem.*, 1994, 33, 6020-6028.; A R Schake, et al., *J. Chem. Soc. Chem. Commun.*, 1992, 181-183.) Just briefly, KMnO$_4$ (6.4 mmol) was added to a slurry of Fe(O$_2$CCH$_3$)$_2$ (16.3 mmol) in 40 mL 60% (v/v) acetic acid/H$_2$O and slowly heated to 60° C. The resulting reddish-brown solution was subsequently cooled to room temperature, layered with 40 mL acetone and allowed to stand undisturbed for several days. The resulting black crystals were collected via vacuum filtration, washed with acetone and dried. IR (cm$^{-1}$): 3441 (br), 1709 (m), 1585 (s), 1421 (s), 3349 (m), 714 (s), 662 (m), 616 (m), 565 (m), 539 (m). Anal calc: C, 20.95; H, 3.52. Found: C, 21.56; H, 3.43. See FIG. 20. The powder X-ray diffraction pattern obtained from the synthesized $Mn_8Fe_4$ is shown in FIG. 21.

NMR Relaxation Studies

Figure 22A:
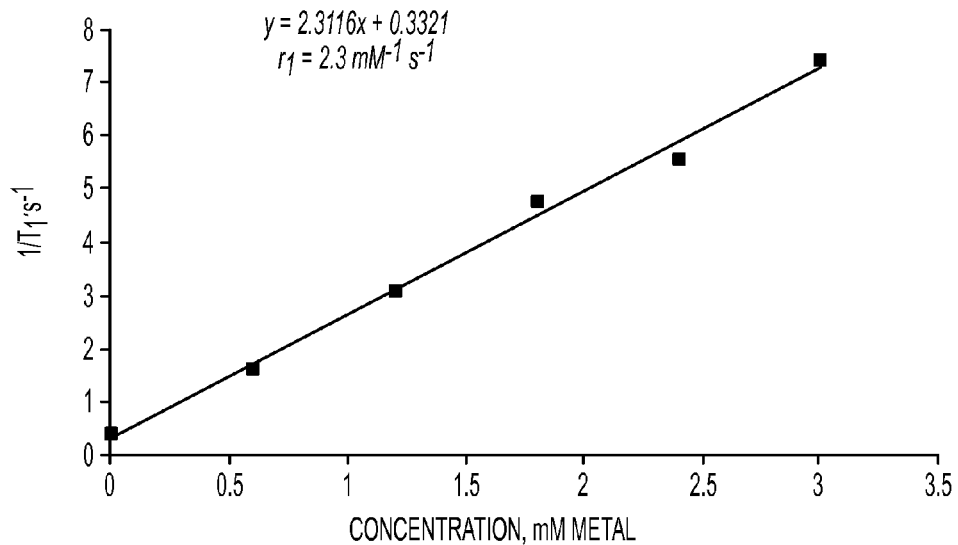
FIG. 22 shows plots of $1/T_1$ (22A) or $1/T_2$ (22B) versus concentration of $Mn_8Fe_4$.
Figure 22B:
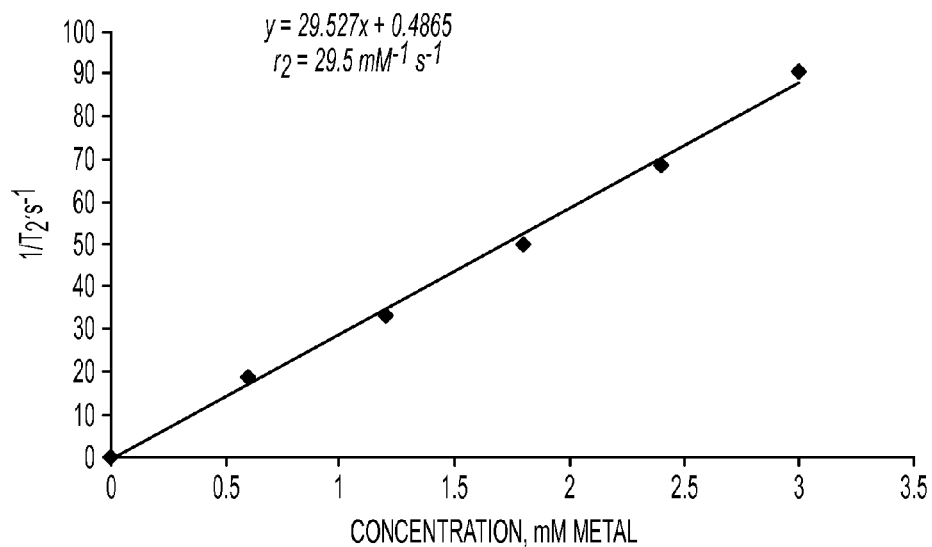

NMR relaxation data were obtained using a Bruker AM 300 MHz spectrometer interfaced with a TecMag DSPect acquisition system. Fresh solutions of $Mn_8Fe_4$ in D$_2$O were prepared (ranging from 0.6 mM metal to 3 mM metal) immediately prior to use. T$_1$ measurements were recorded using the inversion recovery pulse sequence at room temperature with a least squares fit to 10 data points. On the other hand, T$_2$ values were measured using a conventional spin echo sequence. Relaxivity values, $r_1$ and $r_2$, were determined from the slopes of plots of $1/T_1$ (FIG. 22A) or $1/T_2$ (FIG. 22B), respectively, versus concentration of $Mn_8Fe_4$:

$(1/T_i)_{obs}=(1/T_i)_0+r_i[M]$ where $(1/T_i)_{obs}$ is the relaxation rate in the presence of $Mn_8Fe_4$, $(1/T_i)_0$ is the relaxation rate in the absence of $Mn_8Fe_4$, $r_i$ is the relaxivity and [M] is the concentration of $Mn_8Fe_4$ in mM metal.

MRI In Vitro

Figure 23:
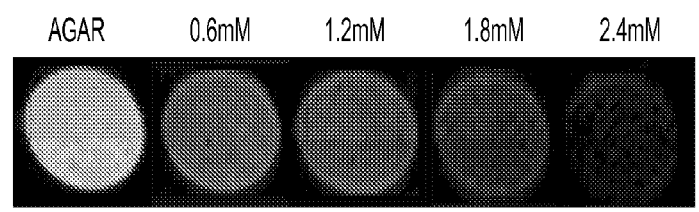
FIG. 23 shows MRI imagining of $Mn_8Fe_4$ clusters in agar as is described in Example 2.

Samples with $Mn_8Fe_4$ concentrations ranging from 0.6 mM metal to 2.4 mM metal were prepared in 3% agar and loaded into phantoms. Imaging was performed on a 7T Bruker Biospin (Germany/USA) imaging console. The protocol used was a spin-echo fast imaging technique. Turbo-RARE-T2 (ParaVision v.4.0 software), with the following set of parameters: echo time (TE) 36 ms, repetition time (TR) 4200 ms, image matrix 256×256, slice thickness 1.0 mm and field of view (FOV) of 8.00 cm. See FIG. 23.

Cytotoxicity Studies

The human prostate cancer derived cell line, DU-145, was used in this study. Cells were split into a six-well plate containing cover slips and maintained in cell culture media at 37° C. Four wells containing the cells were incubated with $Mn_8Fe_4$ (total concentration ranging from 0.006 mM metal to 0.75 mM metal), one well was incubated with iron oxide nanoparticles (Bangs laboratories) for comparison, while another well was left as a control. After 24 hours, cells were trypsinized, followed by dilution (1:5) of a small sample of the cell suspension in 0.4% (w/v) trypan blue stain. The cells (viable and non-viable) were counted using a hemacytometer. The percentage of the viable cells was calculated using the equation below:

$$\% \text{ viability} = \frac{\text{\# of Viable cells counted}}{\text{Total cells counted}} \times 100$$

Figure 24:
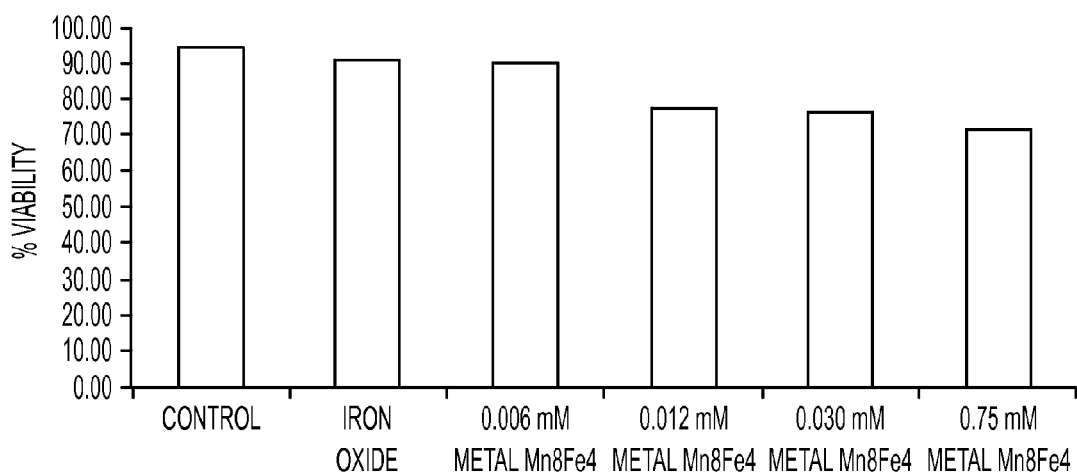
FIG. 24 shows a plot of % viable prostate cancer cells detected in a tryptan blue assay following exposure to various concentrations of $Mn_8Fe_4$ as is described in Example 2.

The results of the cytoxicity studies are plotted in FIG. 24.

What is claimed is:

1. A contrast agent for magnetic resonance imaging comprising: nanoparticles, wherein said nanoparticles comprise:
   a polymer support; and
   a manganese-iron-oxo cluster of formula II:

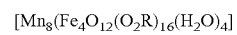

$[Mn_8Fe_4(O_2R)_{16}(H_2O)_4]$    II, or formula III:

$[Mn_8(Fe_4O_{12}(O_2R)_{16}(H_2O)_4]$    III wherein R is selected from the group consisting of alkyl, vinyl, halo, oxy, and oxyalkyl;
   wherein the nanoparticles of the present invention are from about 5 to about 1000 nm in diameter; and
   wherein (i) the polymer support is a carboxylate-coated polymeric bead comprising styrene, vinyl benzoic acid, vinyl alcohol, or a co-polymer thereof and the clusters are bonded to the surface of the carboxylate-coated polymeric bead, or (ii) the polymer support is a co-polymer comprising (a) styrene, vinyl benzoic acid, or vinyl alcohol, and (b) the clusters.

2. The contrast agent of claim 1, wherein the manganese-iron-oxo cluster is a compound of Formula III

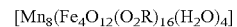

$[Mn_8(Fe_4O_{12}(O_2R)_{16}(H_2O)_4]$    III;

wherein R is selected from the group consisting of alkyl, vinyl, halo, oxy, and oxyalkyl.

3. The contrast agent of claim 2, wherein R is CCH$_3$.

4. The contrast agent of claim 1, wherein the polymer support is a carboxylate-coated polymeric bead comprising styrene, vinyl benzoic acid, vinyl alcohol, or a co-polymer thereof.

5. The contrast agent of claim 1, wherein the carboxylate-coated polymeric bead is a carboxylate-coated polystyrene bead.

6. The contrast agent of claim 1, wherein R is vinyl and the polymer support and clusters together are a co-polymer comprising (a) styrene, vinyl benzoic acid, or vinyl alcohol, and (b) the clusters.

7. The contrast agent of claim 1, wherein the nanoparticle is water soluble.

\* \* \* \* \*